(12) United States Patent
Miraki et al.

(10) Patent No.: US 12,193,661 B2
(45) Date of Patent: *Jan. 14, 2025

(54) SUTURE CLIPS, DEPLOYMENT DEVICES THEREFOR, AND METHODS OF USE

(71) Applicant: Edwards Lifesciences Corporation, Irvine, CA (US)

(72) Inventors: Manouchehr A. Miraki, Laguna Hills, CA (US); Bryan A. Janish, Huntington Beach, CA (US); William T. Biller, Tustin, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 933 days.

This patent is subject to a terminal disclaimer.

(21) Appl. No.: 17/195,143

(22) Filed: Mar. 8, 2021

(65) Prior Publication Data
US 2021/0186489 A1  Jun. 24, 2021

Related U.S. Application Data

(63) Continuation of application No. 15/684,148, filed on Aug. 23, 2017, now Pat. No. 10,939,905.
(Continued)

(51) Int. Cl.
*A61B 17/04* (2006.01)
(52) U.S. Cl.
CPC ...... *A61B 17/0487* (2013.01); *A61B 17/0467* (2013.01); *A61B 17/0469* (2013.01);
(Continued)

(58) Field of Classification Search
CPC ............ A61B 17/0487; A61B 17/0469; A61B 17/0467; A61B 17/29; A61B 17/30;
(Continued)

(56) References Cited

U.S. PATENT DOCUMENTS

| 2,264,679 A | 12/1941 | Ravel |
| 2,516,710 A | 7/1950 | Mascolo |

(Continued)

FOREIGN PATENT DOCUMENTS

| CA | 2141911 | 4/2002 |
| CA | 2141913 | 4/2002 |

(Continued)

*Primary Examiner* — Dianne Dornbusch
(74) *Attorney, Agent, or Firm* — KLARQUIST SPARKMAN, LLP

(57) ABSTRACT

A device for deploying a suture clip onto a suture can include a proximal handle portion that includes an actuation mechanism. The device can also include an outer shaft defining an inner lumen. A crimping assembly can be at least partially disposed within a distal end of the outer shaft. The crimping assembly can include a plurality of crimping members configured to receive and radially compress a suture clip. The actuating mechanism can be configured to move the plurality of crimping members radially inwardly from a first position, where the crimping members are configured to receive a suture clip, to a second position where the plurality of crimping members are configured to radially compress the suture clip, causing the suture clip to plastically deform and become secured around one or more sutures.

24 Claims, 14 Drawing Sheets

Related U.S. Application Data

(60) Provisional application No. 62/380,198, filed on Aug. 26, 2016.

(52) U.S. Cl.
CPC .. *A61B 17/0483* (2013.01); *A61B 2017/0454* (2013.01); *A61B 2017/0488* (2013.01)

(58) Field of Classification Search
CPC .......... A61B 17/221; A61B 2017/0454; A61B 2017/0488; A61B 2017/0409; A61B 2017/042; A61B 2017/0489; A61B 2017/2944; A61B 2017/2902; A61B 2017/2912; A61B 2017/2932; A61B 2017/294
See application file for complete search history.

(56) References Cited

U.S. PATENT DOCUMENTS

| | | |
|---|---|---|
| 2,715,486 A | 8/1955 | Marcoff-Moghadam |
| 2,890,519 A | 6/1959 | Storz |
| 3,143,742 A | 8/1964 | Cromie |
| 3,249,104 A | 5/1966 | Hohnstein |
| 3,274,658 A | 9/1966 | Pile |
| 3,452,742 A | 7/1969 | Muller |
| 3,506,012 A | 4/1970 | Brown |
| 3,509,882 A | 5/1970 | Blake |
| 3,541,591 A | 11/1970 | Hoegerman |
| 3,547,103 A | 12/1970 | Cook |
| 3,570,497 A | 3/1971 | Lemole |
| 3,608,095 A | 9/1971 | Barry |
| 3,638,654 A | 2/1972 | Akuba |
| RE27,391 E | 6/1972 | Merser |
| 3,753,438 A | 8/1973 | Wood et al. |
| 3,859,668 A | 1/1975 | Anderson |
| 3,875,648 A | 4/1975 | Bone |
| 3,898,999 A | 8/1975 | Haller |
| 3,910,281 A | 10/1975 | Kletschka et al. |
| 3,954,109 A | 5/1976 | Patel |
| 3,958,576 A | 5/1976 | Komiya |
| 3,976,079 A | 8/1976 | Samuels et al. |
| 3,988,810 A | 11/1976 | Emery |
| 3,996,623 A | 12/1976 | Kaster |
| 4,038,725 A | 8/1977 | Keefe |
| 4,038,987 A * | 8/1977 | Komiya .................. A61B 17/29 606/221 |
| 4,103,690 A | 8/1978 | Harris |
| 4,140,125 A | 2/1979 | Smith |
| 4,170,990 A | 10/1979 | Baumgart et al. |
| 4,192,315 A | 3/1980 | Hilzinger et al. |
| 4,217,902 A | 8/1980 | March |
| 4,226,239 A * | 10/1980 | Polk ........................ A61F 6/202 128/831 |
| 4,324,248 A | 4/1982 | Perlin |
| 4,345,601 A | 8/1982 | Fukuda |
| 4,393,872 A * | 7/1983 | Reznik .................. A61B 17/29 604/151 |
| 4,416,266 A | 11/1983 | Baucom |
| 4,456,017 A | 6/1984 | Miles |
| 4,471,766 A * | 9/1984 | Terayama ............... A61F 6/208 600/104 |
| 4,485,816 A | 12/1984 | Krumme |
| 4,522,207 A | 6/1985 | Klieman et al. |
| 4,535,764 A | 8/1985 | Ebert |
| 4,548,202 A | 10/1985 | Duncan |
| 4,549,545 A | 10/1985 | Levy |
| 4,586,502 A | 5/1986 | Bedi et al. |
| 4,586,503 A | 5/1986 | Kirsch et al. |
| 4,595,007 A | 6/1986 | Mericle |
| 4,612,932 A | 9/1986 | Caspar et al. |
| 4,637,380 A | 1/1987 | Orejola |
| 4,665,906 A | 5/1987 | Jervis |
| 4,683,895 A | 8/1987 | Pohndorf |
| 4,705,040 A | 11/1987 | Mueller et al. |
| 4,719,924 A | 1/1988 | Crittenden et al. |
| 4,730,615 A | 3/1988 | Sutherland et al. |
| 4,741,330 A | 5/1988 | Hayhurst |
| 4,743,253 A | 5/1988 | Magladry |
| 4,750,492 A | 6/1988 | Jacobs |
| 4,809,695 A | 3/1989 | Gwathmey et al. |
| 4,823,794 A | 4/1989 | Pierce |
| 4,863,460 A | 9/1989 | Magladry |
| 4,873,975 A | 10/1989 | Walsh et al. |
| 4,896,668 A | 1/1990 | Popoff et al. |
| 4,899,744 A | 2/1990 | Fujitsuka et al. |
| 4,901,721 A | 2/1990 | Hakki |
| 4,924,866 A | 5/1990 | Yoon |
| 4,926,860 A | 5/1990 | Stice et al. |
| 4,929,240 A | 5/1990 | Kirsch et al. |
| 4,932,955 A | 6/1990 | Merz et al. |
| 4,950,283 A | 8/1990 | Dzubow et al. |
| 4,950,285 A | 8/1990 | Wilk |
| 4,955,913 A | 9/1990 | Robinson |
| 4,976,715 A | 12/1990 | Bays et al. |
| 4,983,176 A | 1/1991 | Cushman et al. |
| 4,990,152 A | 2/1991 | Yoon |
| 4,997,439 A | 3/1991 | Chen |
| 5,002,550 A | 3/1991 | Li |
| 5,002,562 A | 3/1991 | Oberlander |
| 5,002,563 A | 3/1991 | Pyka et al. |
| 5,026,379 A | 6/1991 | Yoon |
| 5,047,047 A | 9/1991 | Yoon |
| 5,053,047 A | 10/1991 | Yoon |
| 5,070,805 A | 12/1991 | Plante |
| 5,071,431 A | 12/1991 | Sauter et al. |
| 5,074,874 A | 12/1991 | Yoon et al. |
| 5,078,731 A | 1/1992 | Hayhurst |
| 5,100,418 A | 3/1992 | Yoon et al. |
| 5,116,840 A | 5/1992 | Ganguly et al. |
| 5,123,913 A | 6/1992 | Wilk et al. |
| 5,133,735 A * | 7/1992 | Slater ................. A61B 18/1445 606/174 |
| RE34,021 E | 8/1992 | Mueller et al. |
| 5,152,769 A | 10/1992 | Baber |
| 5,154,189 A | 10/1992 | Oberlander |
| 5,158,566 A | 10/1992 | Pianetti |
| 5,163,954 A | 11/1992 | Curcio et al. |
| 5,171,250 A | 12/1992 | Yoon |
| 5,171,251 A | 12/1992 | Bregen et al. |
| 5,171,252 A | 12/1992 | Friedland |
| 5,174,087 A | 12/1992 | Bruno |
| 5,196,022 A | 3/1993 | Bilweis |
| 5,219,358 A | 6/1993 | Bendel et al. |
| 5,222,976 A | 6/1993 | Yoon |
| 5,234,449 A | 8/1993 | Bruker et al. |
| 5,236,440 A | 8/1993 | Hlavacek |
| 5,242,456 A | 9/1993 | Nash et al. |
| 5,246,443 A | 9/1993 | Mai |
| 5,250,056 A * | 10/1993 | Hasson ............... A61B 17/2909 606/208 |
| 5,258,011 A | 11/1993 | Drews |
| 5,258,015 A | 11/1993 | Li et al. |
| 5,269,783 A | 12/1993 | Sander |
| 5,269,809 A | 12/1993 | Hayhurst et al. |
| 5,282,832 A | 2/1994 | Toso et al. |
| 5,290,289 A | 3/1994 | Sanders et al. |
| 5,304,204 A | 4/1994 | Bregen |
| 5,306,280 A | 4/1994 | Bregen et al. |
| 5,306,290 A | 4/1994 | Martins et al. |
| 5,306,296 A | 4/1994 | Wright et al. |
| 5,312,436 A | 5/1994 | Coffey et al. |
| 5,330,503 A | 7/1994 | Yoon |
| 5,336,239 A | 8/1994 | Gimpelson |
| 5,356,424 A | 10/1994 | Buzerak et al. |
| 5,374,268 A | 12/1994 | Sander |
| 5,383,904 A | 1/1995 | Totakura et al. |
| 5,383,905 A | 1/1995 | Golds et al. |
| 5,391,173 A | 2/1995 | Wilk |
| 5,403,346 A | 4/1995 | Loeser |
| 5,409,499 A | 4/1995 | Yi |
| 5,437,680 A | 8/1995 | Yoon |
| 5,437,685 A | 8/1995 | Blasnik |

(56) References Cited

U.S. PATENT DOCUMENTS

| | | |
|---|---|---|
| 5,439,479 A | 8/1995 | Shichman et al. |
| 5,445,167 A | 8/1995 | Yoon et al. |
| 5,450,860 A | 9/1995 | O'Connor |
| 5,452,733 A | 9/1995 | Sterman et al. |
| 5,456,246 A | 10/1995 | Schmieding et al. |
| 5,462,558 A | 10/1995 | Kolesa et al. |
| 5,462,561 A | 10/1995 | Voda |
| 5,474,557 A | 12/1995 | Mai |
| 5,474,572 A | 12/1995 | Hayhurst |
| 5,480,405 A | 1/1996 | Yoon |
| 5,486,197 A | 1/1996 | Le et al. |
| 5,496,336 A | 3/1996 | Cosgrove et al. |
| 5,499,990 A | 3/1996 | Schulken et al. |
| 5,500,000 A | 3/1996 | Feagin et al. |
| 5,520,691 A | 5/1996 | Branch |
| 5,520,702 A | 5/1996 | Sauer et al. |
| 5,527,342 A | 6/1996 | Pietrzak et al. |
| 5,531,763 A | 7/1996 | Mastri et al. |
| 5,545,178 A | 8/1996 | Kensey et al. |
| 5,549,619 A | 8/1996 | Peters et al. |
| 5,562,685 A | 10/1996 | Mollenauer et al. |
| 5,569,274 A | 10/1996 | Rapacki et al. |
| 5,569,301 A | 10/1996 | Granger et al. |
| 5,582,616 A | 12/1996 | Bolduc et al. |
| 5,582,619 A | 12/1996 | Ken |
| 5,586,983 A | 12/1996 | Sanders et al. |
| 5,591,179 A | 1/1997 | Edelstein |
| 5,593,414 A | 1/1997 | Shipp et al. |
| 5,593,424 A | 1/1997 | Northrup, III |
| 5,609,608 A | 3/1997 | Benett et al. |
| 5,626,590 A | 5/1997 | Wilk |
| 5,630,824 A | 5/1997 | Hart |
| 5,632,752 A | 5/1997 | Buelna |
| 5,632,753 A | 5/1997 | Loeser |
| 5,643,289 A | 7/1997 | Sauer et al. |
| 5,643,295 A | 7/1997 | Yoon |
| 5,645,553 A | 7/1997 | Kolesa et al. |
| 5,645,568 A | 7/1997 | Chervitz et al. |
| 5,665,109 A | 9/1997 | Yoon |
| 5,669,917 A | 9/1997 | Sauer et al. |
| 5,669,935 A | 9/1997 | Rosenman et al. |
| 5,681,351 A | 10/1997 | Jamiolkowski et al. |
| 5,683,417 A | 11/1997 | Cooper |
| 5,695,505 A | 12/1997 | Yoon |
| 5,697,943 A | 12/1997 | Sauer et al. |
| 5,700,270 A | 12/1997 | Peyser et al. |
| 5,700,271 A | 12/1997 | Whitfield et al. |
| 5,707,380 A | 1/1998 | Hinchliffe et al. |
| 5,709,693 A | 1/1998 | Taylor |
| 5,709,695 A | 1/1998 | Northrup, III |
| 5,725,539 A | 3/1998 | Matern |
| 5,725,542 A * | 3/1998 | Yoon ..................... A61B 17/12 606/151 |
| 5,725,556 A | 3/1998 | Moser et al. |
| 5,728,135 A | 3/1998 | Bregen et al. |
| 5,735,290 A | 4/1998 | Sterman et al. |
| 5,735,877 A | 4/1998 | Pagedas |
| 5,766,183 A | 6/1998 | Sauer |
| 5,776,188 A | 7/1998 | Shepherd et al. |
| 5,799,661 A | 9/1998 | Boyd et al. |
| 5,810,851 A | 9/1998 | Yoon |
| 5,810,882 A | 9/1998 | Bolduc et al. |
| 5,820,631 A | 10/1998 | Nobles |
| 5,824,008 A | 10/1998 | Bolduc et al. |
| 5,830,221 A | 11/1998 | Stein et al. |
| 5,833,696 A | 11/1998 | Whitfield et al. |
| 5,845,645 A | 12/1998 | Bonutti |
| 5,849,019 A | 12/1998 | Yoon |
| 5,861,004 A | 1/1999 | Kensey et al. |
| 5,879,371 A | 3/1999 | Gardiner et al. |
| 5,891,130 A | 4/1999 | Palermo et al. |
| 5,891,160 A | 4/1999 | Williamson, IV et al. |
| 5,895,393 A | 4/1999 | Pagedas |
| 5,895,394 A | 4/1999 | Kienzle et al. |
| 5,919,207 A | 7/1999 | Taheri |
| 5,948,001 A | 9/1999 | Larsen |
| 5,961,481 A | 10/1999 | Sterman et al. |
| 5,961,539 A | 10/1999 | Northrup, III et al. |
| 5,964,772 A | 10/1999 | Bolduc et al. |
| 5,967,985 A | 10/1999 | Hayakawa |
| 5,972,024 A | 10/1999 | Northrup, III et al. |
| 5,976,159 A | 11/1999 | Bolduc et al. |
| 5,984,917 A | 11/1999 | Fleischman et al. |
| 5,989,242 A | 11/1999 | Saadat et al. |
| 5,989,268 A | 11/1999 | Pugsley, Jr. et al. |
| 5,997,556 A | 12/1999 | Tanner |
| 6,001,110 A | 12/1999 | Adams |
| 6,013,084 A | 1/2000 | Ken et al. |
| 6,015,428 A | 1/2000 | Pagedas |
| 6,039,176 A | 3/2000 | Wright |
| 6,066,160 A | 5/2000 | Colvin et al. |
| 6,074,409 A | 6/2000 | Goldfarb |
| 6,120,524 A | 9/2000 | Taheri |
| 6,132,438 A | 10/2000 | Fleischman et al. |
| 6,139,540 A | 10/2000 | Rost et al. |
| 6,143,004 A | 11/2000 | Davis et al. |
| 6,146,329 A | 11/2000 | Hayakawa |
| 6,176,413 B1 | 1/2001 | Heck et al. |
| 6,190,373 B1 | 2/2001 | Palermo et al. |
| 6,193,733 B1 | 2/2001 | Adams |
| 6,193,734 B1 | 2/2001 | Bolduc et al. |
| 6,231,592 B1 | 5/2001 | Bonutti et al. |
| 6,241,765 B1 | 6/2001 | Griffin et al. |
| 6,254,615 B1 | 7/2001 | Bolduc et al. |
| 6,306,141 B1 | 10/2001 | Jervis |
| 6,346,112 B2 | 2/2002 | Adams |
| 6,368,334 B1 | 4/2002 | Sauer |
| 6,432,123 B2 | 8/2002 | Schwartz et al. |
| 6,475,230 B1 | 11/2002 | Bonutti et al. |
| 6,508,829 B1 | 1/2003 | Levinson et al. |
| 6,514,265 B2 | 2/2003 | Ho et al. |
| 6,533,796 B1 | 3/2003 | Sauer et al. |
| 6,537,290 B2 | 3/2003 | Adams et al. |
| 6,551,332 B1 | 4/2003 | Nguyen et al. |
| 6,589,279 B1 | 7/2003 | Anderson et al. |
| 6,607,541 B1 | 8/2003 | Gardiner et al. |
| 6,613,059 B2 | 9/2003 | Schaller et al. |
| 6,626,930 B1 | 9/2003 | Allen et al. |
| 6,641,592 B1 | 11/2003 | Sauer et al. |
| 6,641,593 B1 | 11/2003 | Schaller et al. |
| 6,682,540 B1 | 1/2004 | Sancoff et al. |
| 6,719,767 B1 | 4/2004 | Kimblad |
| 6,746,457 B2 | 6/2004 | Dana et al. |
| 6,749,622 B2 | 6/2004 | McGuckin, Jr. et al. |
| 6,776,784 B2 | 8/2004 | Ginn |
| 6,860,890 B2 | 3/2005 | Bachman et al. |
| 6,896,686 B2 | 5/2005 | Weber |
| 6,913,607 B2 | 7/2005 | Ainsworth et al. |
| 6,918,917 B1 | 7/2005 | Nguyen et al. |
| 6,921,407 B2 | 7/2005 | Nguyen et al. |
| 6,926,730 B1 | 8/2005 | Nguyen et al. |
| 6,945,980 B2 | 9/2005 | Nguyen et al. |
| 6,960,221 B2 | 11/2005 | Ho et al. |
| 7,011,669 B2 | 3/2006 | Kimblad |
| 7,083,628 B2 | 8/2006 | Bachman |
| 7,094,244 B2 | 8/2006 | Schreck |
| 7,112,207 B2 | 9/2006 | Allen et al. |
| 7,220,266 B2 | 5/2007 | Gambale |
| 7,235,086 B2 | 6/2007 | Sauer et al. |
| 7,264,625 B1 | 9/2007 | Buncke |
| 7,381,210 B2 | 6/2008 | Zarbatany et al. |
| 7,628,797 B2 | 12/2009 | Tieu et al. |
| 7,731,727 B2 | 6/2010 | Sauer |
| 7,833,237 B2 | 11/2010 | Sauer |
| 7,842,051 B2 | 11/2010 | Dana et al. |
| 7,862,584 B2 | 1/2011 | Lyons et al. |
| 7,875,056 B2 | 1/2011 | Jervis et al. |
| 7,959,674 B2 | 6/2011 | Shu et al. |
| 7,981,139 B2 | 7/2011 | Martin et al. |
| 8,021,421 B2 | 9/2011 | Fogarty et al. |
| 8,100,923 B2 | 1/2012 | Paraschac et al. |
| 8,105,355 B2 | 1/2012 | Page et al. |
| 8,252,005 B2 | 8/2012 | Findlay, III et al. |
| 8,398,657 B2 | 3/2013 | Sauer |

(56) References Cited

U.S. PATENT DOCUMENTS

| | | |
|---|---|---|
| 8,398,680 B2 | 3/2013 | Sauer et al. |
| 8,425,555 B2 | 4/2013 | Page et al. |
| 8,480,686 B2 | 7/2013 | Bakos et al. |
| 8,753,373 B2 | 6/2014 | Chau et al. |
| 9,017,347 B2 | 4/2015 | Oba et al. |
| 9,592,048 B2 | 3/2017 | Moehle et al. |
| 2003/0109922 A1 | 6/2003 | Peterson et al. |
| 2003/0195563 A1 | 10/2003 | Foerster |
| 2003/0204205 A1 | 10/2003 | Sauer et al. |
| 2003/0233105 A1 | 12/2003 | Gayton |
| 2004/0181238 A1 | 9/2004 | Zarbatany et al. |
| 2004/0204724 A1 | 10/2004 | Kissel et al. |
| 2004/0249414 A1 | 12/2004 | Kissel et al. |
| 2005/0251209 A1 | 11/2005 | Saadat et al. |
| 2006/0047314 A1 | 3/2006 | Green |
| 2006/0079913 A1 | 4/2006 | Whitfield et al. |
| 2006/0089571 A1 | 4/2006 | Gertner |
| 2006/0184203 A1 | 8/2006 | Martin et al. |
| 2006/0265010 A1 | 11/2006 | Paraschac et al. |
| 2006/0276871 A1 | 12/2006 | Lamson et al. |
| 2006/0282119 A1 | 12/2006 | Perchik |
| 2007/0005079 A1 | 1/2007 | Zarbatany et al. |
| 2007/0005081 A1 | 1/2007 | Findlay et al. |
| 2007/0049952 A1 | 3/2007 | Weiss |
| 2007/0049970 A1 | 3/2007 | Belef et al. |
| 2007/0088391 A1 | 4/2007 | McAlexander et al. |
| 2007/0179530 A1 | 8/2007 | Tieu et al. |
| 2007/0270907 A1 | 11/2007 | Stokes et al. |
| 2008/0015437 A1 | 1/2008 | Hongou |
| 2008/0154286 A1 | 6/2008 | Abbott et al. |
| 2008/0255591 A1 | 10/2008 | Harada et al. |
| 2008/0281356 A1 | 11/2008 | Chau et al. |
| 2008/0294037 A1 | 11/2008 | Richter |
| 2009/0143821 A1 | 6/2009 | Stupak |
| 2009/0281377 A1 | 11/2009 | Newell et al. |
| 2010/0001038 A1 | 1/2010 | Levin et al. |
| 2010/0076462 A1 | 3/2010 | Bakos et al. |
| 2010/0324597 A1 | 12/2010 | Shikhman |
| 2011/0087241 A1 | 4/2011 | Nguyen |
| 2011/0087242 A1 | 4/2011 | Pribanic et al. |
| 2011/0105903 A1 | 5/2011 | Ohnuma |
| 2011/0224714 A1 | 9/2011 | Gertner |
| 2011/0251641 A1 | 10/2011 | Sauer et al. |
| 2011/0283514 A1 | 11/2011 | Fogarty et al. |
| 2012/0089182 A1 | 4/2012 | Page et al. |
| 2012/0102526 A1 | 4/2012 | Lejeune |
| 2013/0053884 A1 | 2/2013 | Roorda |
| 2013/0110164 A1 | 5/2013 | Milazzo et al. |
| 2013/0158600 A1 | 6/2013 | Conklin et al. |
| 2013/0165953 A1 | 6/2013 | Oba et al. |
| 2013/0282028 A1 | 10/2013 | Conklin et al. |
| 2014/0031864 A1 | 1/2014 | Jafari et al. |

FOREIGN PATENT DOCUMENTS

| | | |
|---|---|---|
| CN | 255833 | 8/2002 |
| DE | 69512446 T2 | 5/2000 |
| DE | 69612447 T2 | 7/2001 |
| EP | 0453251 A1 | 10/1991 |
| EP | 0669101 A1 | 8/1995 |
| EP | 0669103 A1 | 8/1995 |
| EP | 1484023 B1 | 12/2004 |
| GB | 2287319 A | 9/1995 |
| WO | 01049207 A2 | 7/2001 |
| WO | 0166001 A2 | 9/2001 |
| WO | 2004/024006 A1 | 3/2004 |
| WO | 2015006739 A1 | 1/2015 |
| WO | 2015183749 A1 | 12/2015 |

\* cited by examiner

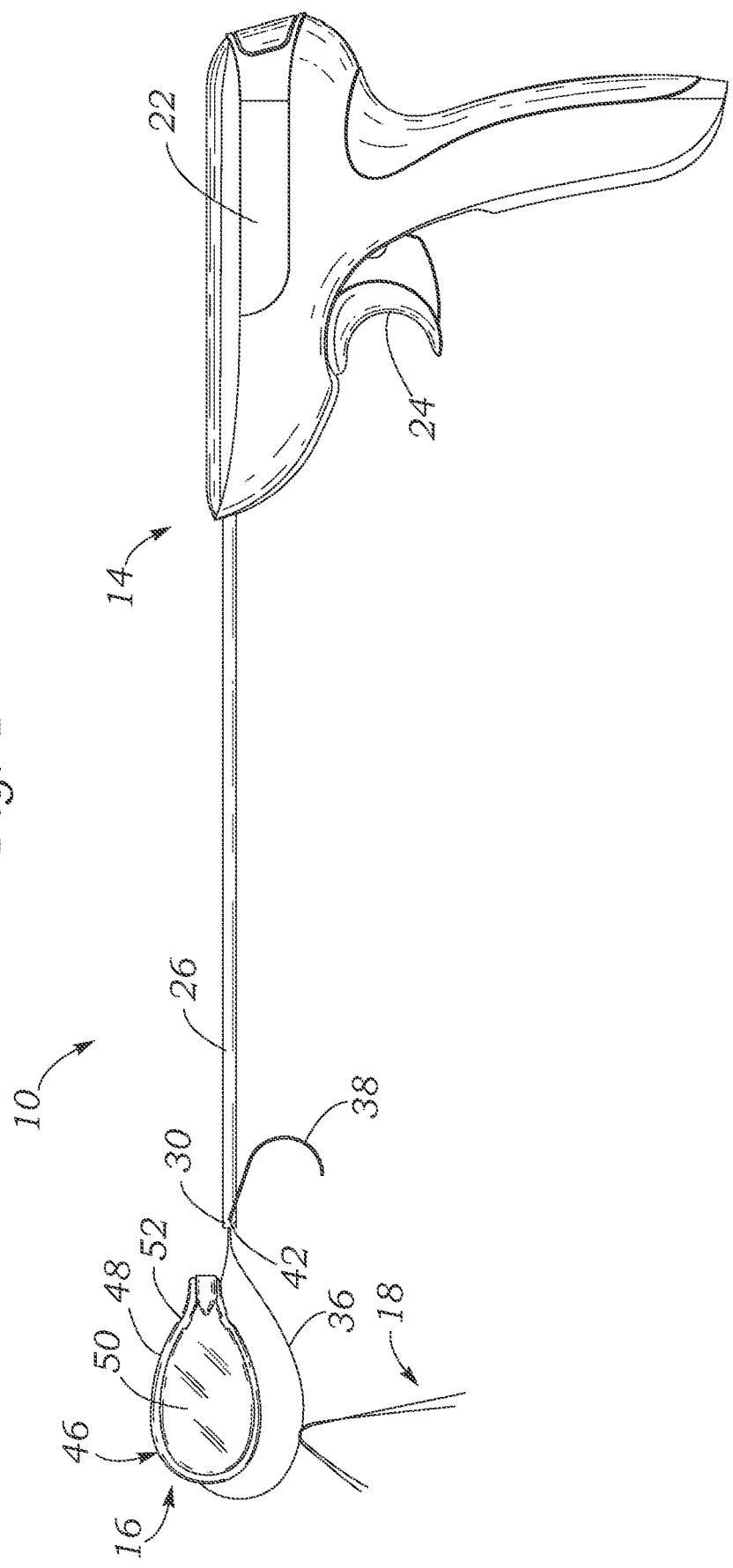

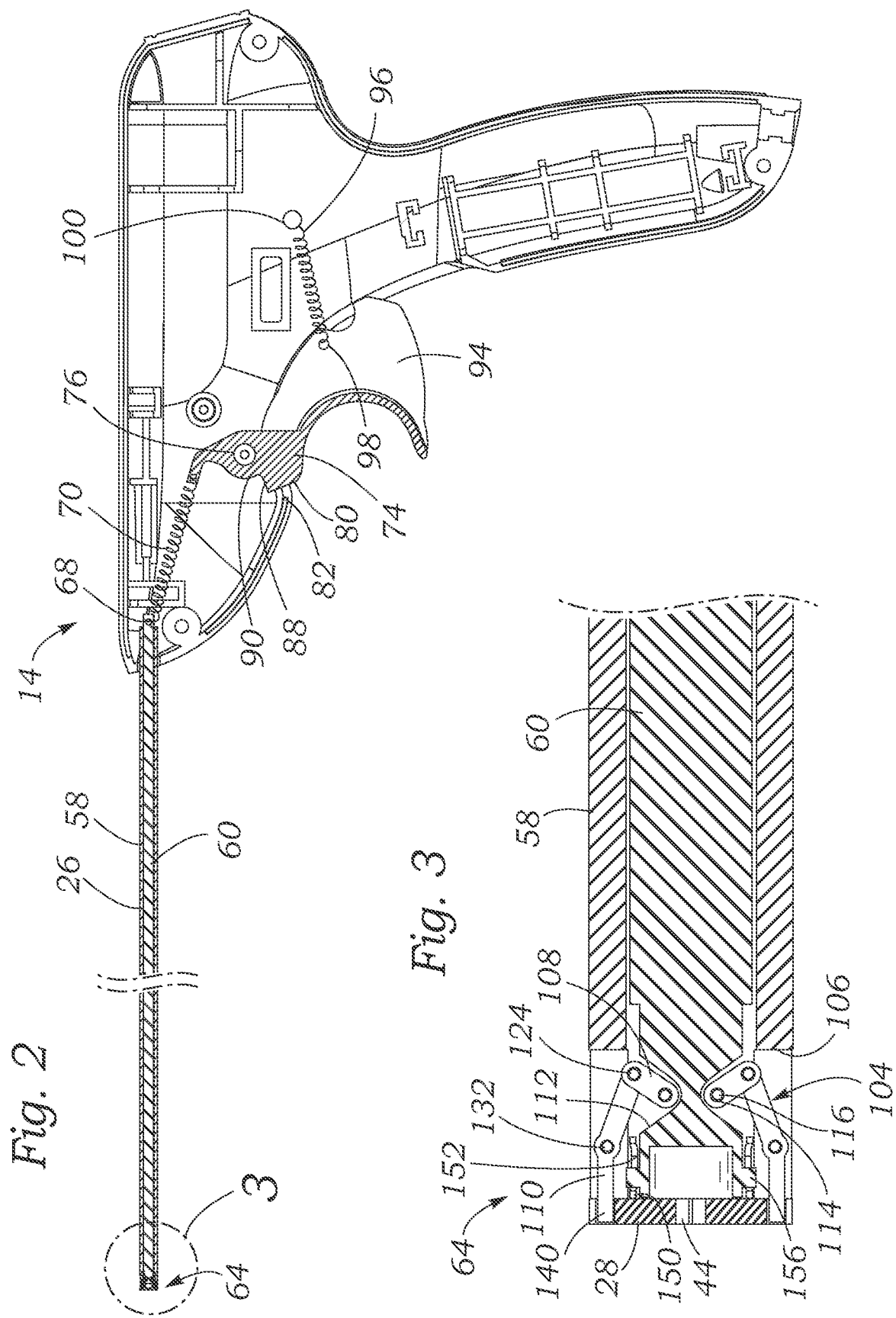

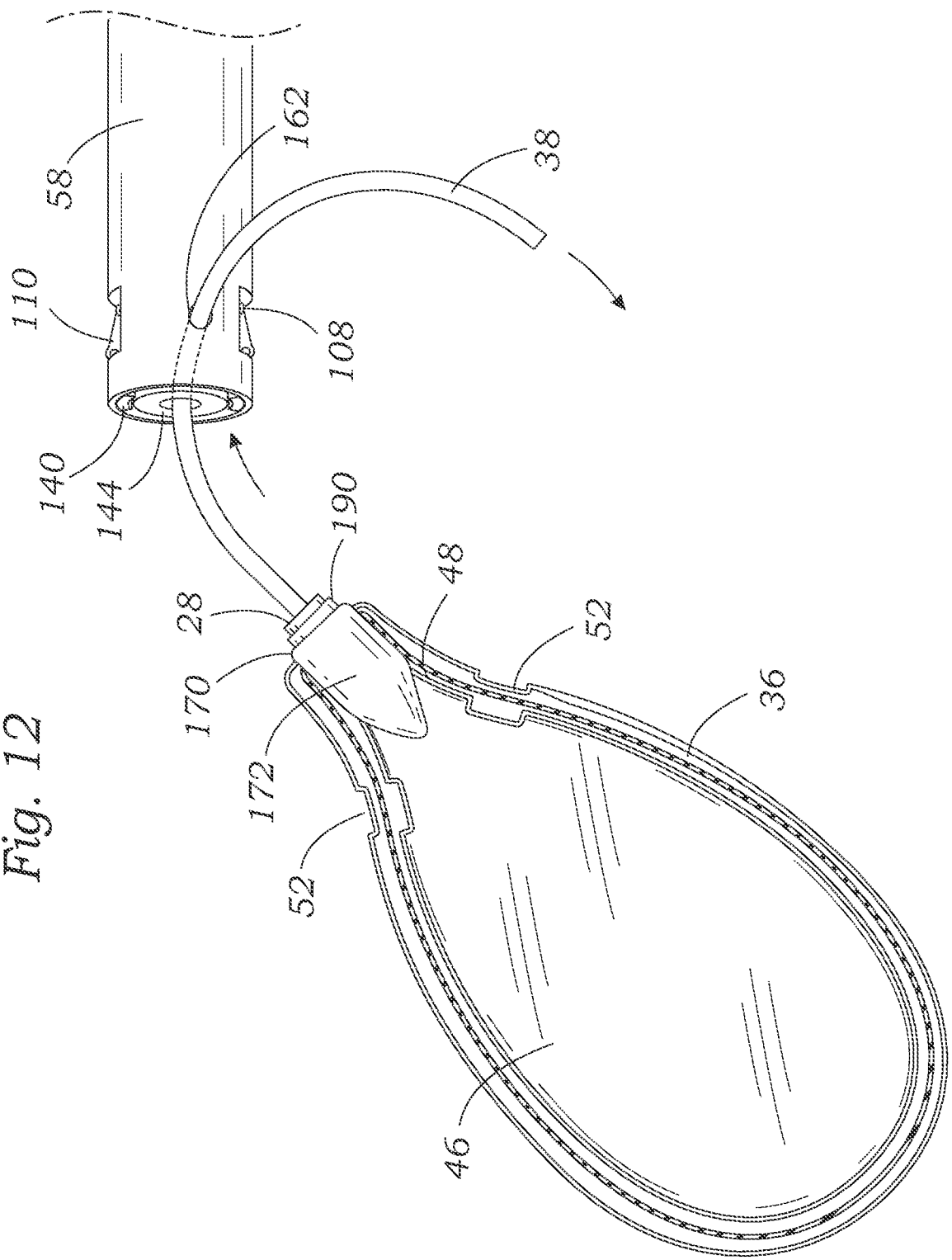

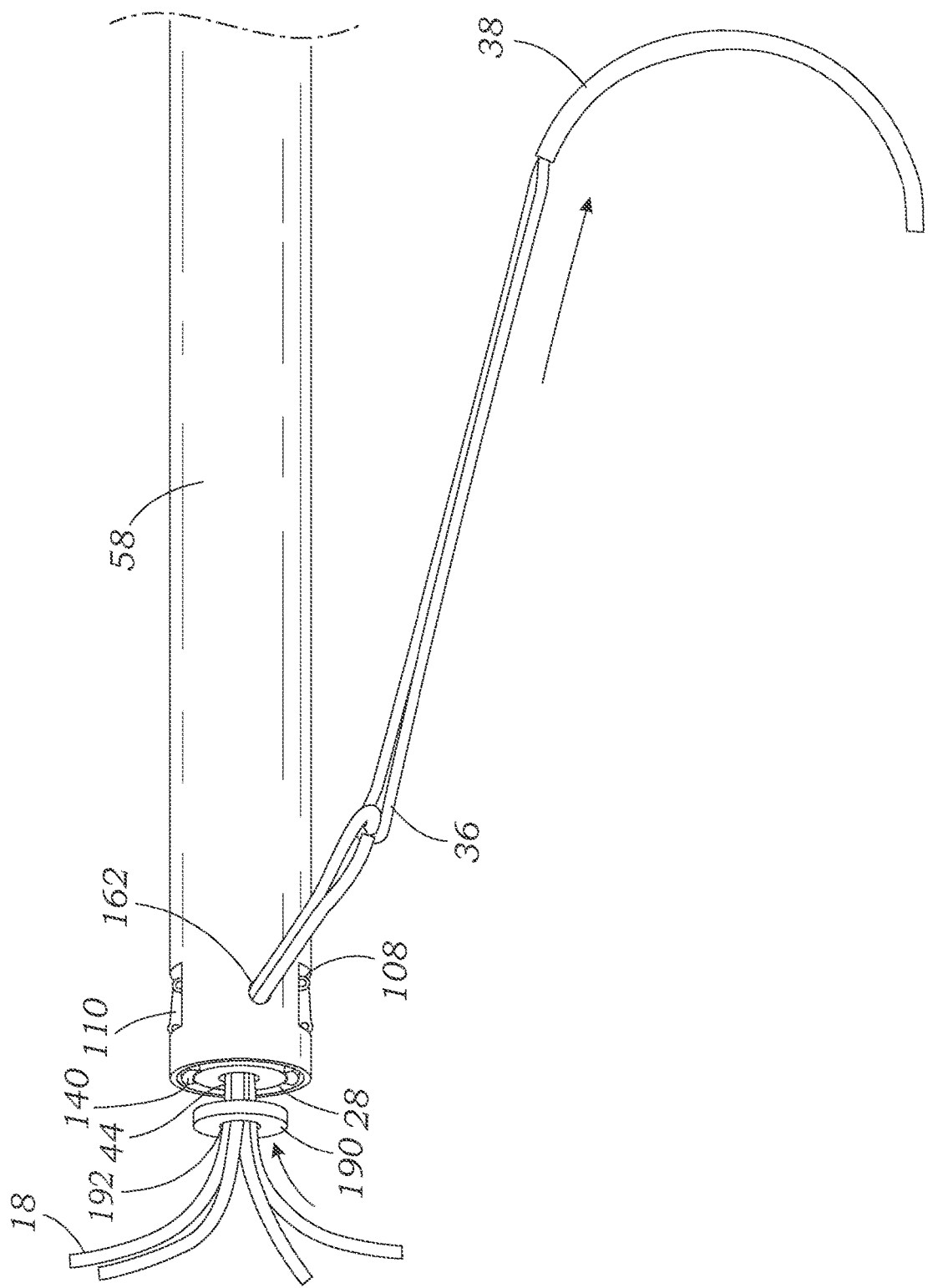

SUTURE CLIPS, DEPLOYMENT DEVICES THEREFOR, AND METHODS OF USE

CROSS-REFERENCE TO RELATED APPLICATION

This application is a continuation of U.S. patent application Ser. No. 15/684,148, filed Aug. 23, 2017, now U.S. Pat. No. 10,939,905, which claims the benefit of U.S. Patent Application No. 62/380,198, filed Aug. 26, 2016. The entire disclosure of each of these prior applications is incorporated by reference for all purposes.

FIELD

This disclosure relates generally to suture clips, and to devices and methods for securing sutures using suture clips.

BACKGROUND

Sutures are used for a variety of surgical purposes, such as approximation of tissue and ligation of tissue. When placing sutures, the strand of suture material to be used typically has a needle affixed to one end which is passed (looped) through the tissue to be approximated or ligated, forming a stitch. The stitch is then tensioned appropriately, and the two free ends of the suture loop, the needle end and the non-needle end, are knotted to retain the desired tension in the stitch. Forming knots in sutures during open surgery is a simple matter, though time-consuming, but forming knots in sutures during endoscopic surgery can require two surgeons to cooperate in a multi-step process that is performed with multiple instruments to pass the needle and suture back and forth to tie the suture knot.

Suture locking devices that eliminate the need to tie knots in order to speed up surgical procedures are known. Suture retainers or locks are used in place of suture knots to prevent passage of a suture end into and through tissue and to maintain the tension applied to the suture material during a suturing procedure.

When using a method that employs a clip to secure the suture, the clip can be delivered by advancing the clip along a suture line to the area of interest, and then deploying the clip such that the clip secures the suture in place. With the clip thus secured, the excess suture can be cut and removed from the patient. An example of such a clip, as well as methods and devices for use therewith, are disclosed in U.S. Patent Application Publication No. 2007/0005081 A1 and U.S. Pat. No. 7,628,797, the entire contents of which are expressly incorporated by reference herein.

Despite the existence of knotless suture locking devices in the art, there is a need for improved devices that enable easy access to the suture, accurate tensioning of the suture, and are simple to use. In light of the foregoing, there is presently a need for improved systems for securing sutures with clips.

SUMMARY

Disclosed herein are improved suture-clip delivery devices and systems, suture clips that can be used therewith, and their methods of use. The methods can be used, for example, in securing heart valve repair or replacement prostheses in or near the heart. The devices and methods are particularly well suited for traditional surgery or minimally invasive surgery. The devices disclosed herein can eliminate the need for surgical knots, thus reducing surgical time and exposure. Further, the devices can improve the ease of implantation because the clinician need not tie knots in the limited space in and around the heart.

Some embodiments of suture clip delivery systems described herein utilize a suture clip having a body with an at least generally flat shape, such as a flat circular or elliptical suture clip, with a suture aperture formed therein, and a handheld device for deploying one or more suture clips. An inner lumen formed in a distal end of the device and the suture aperture of the suture clip can be sized and configured so that one or more lines of suture may pass therethrough. The suture aperture of the suture clip can have an open configuration, wherein the suture aperture is generally unobstructed, and a closed, or crimped, configuration, wherein the suture clip has been plastically deformed so as to frictionally engage the suture line(s) passing therethrough and to prevent them from moving in one or more directions.

In a particular embodiment, a suture clip delivery device can include a proximal handle portion that includes an actuation mechanism, such as a trigger. The device can include an outer shaft defining an inner lumen. A crimping assembly can be disposed at least partially within a distal end of the outer shaft. The crimping assembly can be configured to apply a distributed, such as an evenly distributed, radially compressive force to a suture clip. For example, the crimping assembly can be configured to plastically deform the suture clip such that the suture aperture is closed, at least substantially closed, or otherwise secures the suture line(s), while reducing or eliminating bending or buckling of the axial suture clip surfaces.

In one implementation, the crimping assembly can include a plurality of crimping members configured to receive and radially compress a suture clip. The actuation mechanism can be configured to move the plurality of crimping members radially inwardly from a first position where the crimping members are configured to receive a suture clip to a second position where the plurality of crimping members are configured to radially compress the suture clip, causing the suture clip to plastically deform.

In some implementations, the suture clip delivery device can include an inner shaft at least partially disposed within the inner lumen of the outer shaft. The inner shaft or outer shaft can be moveable with respect to the other, such as by use of the actuation mechanism. For example, the actuation mechanism can be configured to move the inner shaft axially, proximally or distally, relative to the outer shaft.

The plurality of crimping members, in some implementations, can be articulated. For example, each of the plurality of crimping members can include an inner hinge member pivotably coupled to an outer hinge member. In a specific example, the inner hinge members can be coupled to an inner shaft of the suture clip delivery device and the outer hinge members can be coupled to the outer shaft of the suture clip delivery device. In further implementations, the plurality of crimping members can be disposed proximate to opposing sides of the distal end of the outer shaft. According to another implementation, each of the plurality of crimping members can include a distal jaw portion configured to receive and radially compress a suture clip.

In another aspect, the crimping assembly can include a cutting member configured to sever one or more sutures. In one example, the cutting member can include an annular body defining axial and radial apertures for receiving the one or more sutures. In another example, the suture clip delivery device can include an inner shaft at least partially disposed within the lumen of the outer shaft. The inner shaft can define a pair of radially extending pegs. A radial surface of the cutting member can define a plurality of positioning apertures configured to receive the pegs and an inner suture aperture configured to receive the one or more sutures.

The cutting member can be disposed about the inner shaft, such that the pegs are received within the positioning apertures. The positioning apertures can have an axial length larger than the diameter of the pegs, such that the cutting member is axially moveable from a first position where the inner suture aperture and an outer suture aperture formed in the outer shaft are aligned to a second position where the inner suture aperture and the outer suture aperture are at least substantially not aligned.

In another implementation, the distal end of the outer shaft can define an axially recessed portion configured to receive a suture clip.

In a further aspect, the present disclosure provides a suture clip delivery assembly. The suture clip delivery assembly can include a suture clip delivery device, such as a suture clip delivery device as described above. The suture clip delivery assembly can further include a suture clip and a suture snare assembly. The suture snare assembly can include a suture snare coupled to a handle. The handle can be configured to be inserted through an aperture formed in a distal end of an outer shaft of the suture clip delivery device and through an aperture formed in a radial surface of the outer shaft. The suture snare assembly can further include a retaining member configured to releasably retain the suture snare. In some examples, the retaining member can define a groove, such as a groove formed in a perimeter surface of the retaining member, for receiving the suture snare. In further examples, the retaining member can define one or more notches for helping to release the suture snare from engagement with the retaining member.

In another aspect, the present disclosure provides a method for deploying a suture clip onto a suture. A suture clip can be received within a crimping mechanism positioned at a distal end portion of a suture clip deployment device. A free end of the suture can be passed through an aperture formed in the suture clip. A free end of the suture can be passed into a distal end portion of an inner lumen of an outer shaft of the suture clip deployment device. The crimping mechanism can apply a distributed, radially compressive force to the suture clip to plastically deform the suture clip and reduce the aperture to secure the suture within the suture clip. For example, the distributed, radially compressive force can be applied in at least two directions, such as to at least two opposing radial surfaces of the suture clip. In some cases, a distributed force can be sufficient to reduce an aperture of the suture clip, while reducing or eliminating bending or buckling of the axial surfaces of the suture clip.

In particular implementations, the suture clip can be radially compressed with a plurality of crimping members coupled to the suture clip deployment device. In some examples, radially compressing the suture clip with a plurality of crimping members can include radially compressing the suture clip at least at opposing radial sides. In another example, radially compressing the suture clip with a plurality of crimping members can include moving an inner shaft or the outer shaft of the suture clip deployment device axially with respect to the other, causing the plurality of crimping members to radially compress the suture clip to secure the suture.

In a further example, the plurality of crimping members can be configured to be actuated from a first position where the plurality of crimping members do not plastically deform the suture clip to a second position where the plurality of crimping members plastically deform the suture clip. For instance, when in the second position, the plurality of crimping members can apply a radially inwardly directed force to plastically deform the suture clip, such that an aperture formed in the suture clip can frictionally engage and secure one or more suture lines passing therethrough. In another example, in the first position, the plurality of crimping members can apply a radially inwardly directed force to the suture clip sufficient to secure the suture clip within the plurality of crimping members.

The method, in yet further implementations, can include severing one or more suture lines proximate the suture clip, such as proximate a proximal end of the suture clip. For example, the method can include axially moving a cutting member relative to the outer shaft. In a specific example, the one or more suture lines can extend through an aperture formed in the suture clip, through an inner suture aperture formed in the cutting member that is selectively alignable with an outer suture aperture formed in the outer shaft of the suture clip deployment device, and through the outer suture aperture. The suture clip deployment device can be selectively actuated from a first position where the inner and outer suture apertures are at least substantially aligned to a second position where the inner and outer sutures apertures are offset and sever the one or more suture lines passing therethrough.

In a further embodiment, the present disclosure provides a suture retaining device, such as a suture clip, that includes a suture retaining body that defines an outer surface and a suture aperture configured to receive and frictionally engage one or more sutures passing therethrough. The suture retaining device can include an atraumatic or biocompatible coating disposed on at least a portion of the outer surface of the suture retaining body.

In particular implementations, the suture retaining device, such as a suture clip, can be formed from a plastically deformable material. In some examples, the suture retaining device can be a flat suture clip, such as a flat suture clip having an at least generally circular or elliptical shape. For example, the suture clip can be disk-shaped.

In further implementations, the atraumatic or biocompatible coating is a biocompatible coating that can include one or more of heparin, an extracellular matrix, or one or more components of an extracellular matrix. In another implementation, the atraumatic or biocompatible coating is an atraumatic coating that can include one or more of a siloxane polymer, an olefin-based polymer, a copolymer, or a fluorinated polymer. In a specific example, the coating can be a felt, such as an expanded polytetrafluoroethylene felt. In further implementations, the atraumatic or biocompatible coating can encapsulate all or a portion of the suture retaining device, such as within a pillow of encapsulating material. For example, the coating can be coupled to the suture retaining body at least about the edges of the suture aperture such that the encapsulation does not obstruct suture access to the suture aperture.

The foregoing and other objects, features, and advantages of the disclosed technology will become more apparent from the following detailed description, which proceeds with reference to the accompanying figures.

BRIEF DESCRIPTION OF THE DRAWINGS

FIG. 1 is an elevational view of an embodiment of a suture clip delivery assembly, including a suture clip delivery device and a suture snare assembly.

FIG. 2 is a cross-sectional view of the suture clip delivery device of FIG. 1.

FIG. 3 is a detail view of a crimping assembly portion of the suture clip delivery device of FIG. 2.

FIG. 12 is a perspective view illustrating the loading of a spacer and a suture clip into a suture clip delivery device using a suture snare assembly.

FIG. 13 is a perspective view illustrating the threading of a suture through a spacer and a suture clip loaded into a suture clip delivery device using a suture snare.

DETAILED DESCRIPTION

Figure 4:
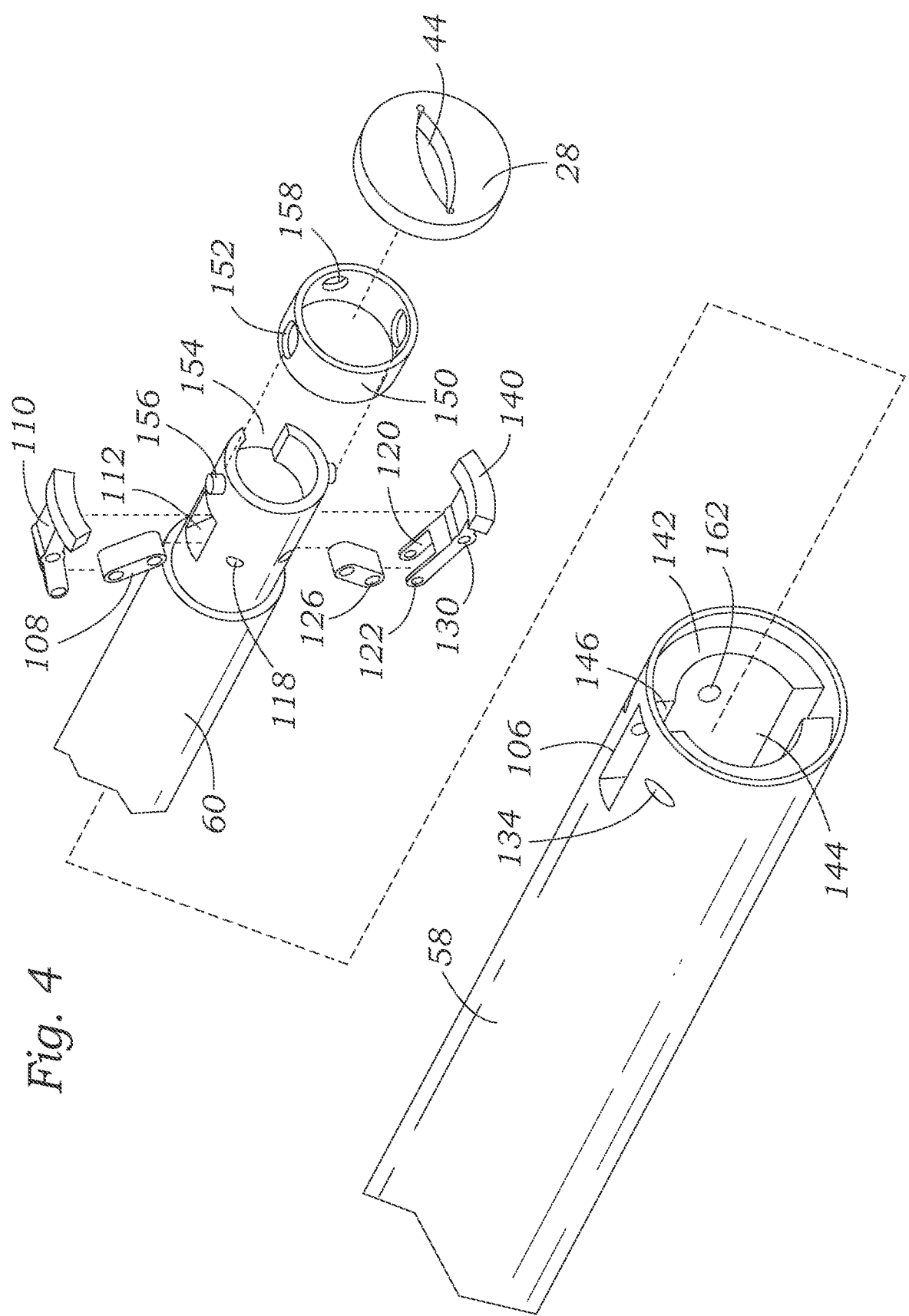
FIG. 4 is an exploded view of a crimping assembly portion of the suture clip delivery device of FIG. 1.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment, or example of the present disclosure are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The present disclosure is not restricted to the details of any disclosed embodiment. The present disclosure extends to any novel one, or any novel combination, of the features disclosed in this specification (including any accompanying claims, abstract, and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, systems, and apparatus can be used in conjunction with other systems, methods, and apparatus.

As used herein, the terms "a," "an," and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C," or "A, B, and C."

As used herein, the term "coupled" generally means physically, magnetically, electrically, or chemically, coupled or linked and does not exclude the presence of intermediate elements between the coupled items absent specific contrary language. Components may be "directly coupled," in which case the directly coupled components are linked without the presence of intermediate elements.

Described herein are suture clips, and devices and methods for securing sutures with suture clips. FIGS. 1-10 illustrate an embodiment of a suture clip delivery assembly 10 that includes a suture clip deployment device 14 that can be loaded with a suture clip 28, such as one of the disc-shaped suture clips shown in FIGS. 14A-14E. While any of the disclosed suture clips can be used to secure a single suture, or can be used to secure plural sutures or suture segments at the same time, this description proceeds with reference to non-limiting examples wherein each suture clip is deployed onto two sutures segments for ease of description only.

FIG. 1 shows an example of a suture clip delivery assembly 10 according to one embodiment of the present disclosure. The suture clip delivery assembly 10 can include two main components: a suture clip delivery device or apparatus 14 and a suture snare assembly 16. The suture snare assembly 16 can be used to thread a suture 18 into the suture clip delivery device 14.

The suture clip delivery device 14 can include a handle portion 22 including a trigger or actuator 24. An elongate shaft 26 can extend distally from the handle portion 22, and the proximal end of the elongate shaft 26 can be coupled to the handle portion 22. In particular implementations, the proximal end of the elongate shaft 26 can be disposed within the handle portion 22. A suture clip 28 (FIG. 4) can be disposed within a recess formed within the distal end 30 of the elongate shaft 26.

The suture snare assembly 16 can include a suture snare 36, such as looped length of wire. In particular examples, the suture snare 36 can be formed from a biocompatible flexible material including metals, such as stainless steel, for example 304 stainless steel, a nickel titanium alloy ("nitinol"), or other metals or alloys. In other implementations, the suture snare 36 can be formed from a polymeric material, such as polypropylene, or a natural fiber material. The suture snare 36 can be coupled to a handle 38. The handle 38 can be curved or otherwise shaped to facilitate grasping or manipulation by a physician. The handle 38 can be made of any suitable material, including metals, such as stainless steel, or suitably rigid plastics.

The handle 38 can be configured to be inserted through one or more apertures 42 formed in the distal end 30 of the elongate shaft 26. The suture snare 36 can pass through an aperture 44 (FIG. 4) formed in the suture clip 28. Thus, if the handle 38 is moved radially outwardly from the elongate shaft 26, the suture snare can be drawn through the aperture 44, through the lumen of the elongate shaft 26, and radially outwardly from the aperture 42 formed in the elongate shaft 26.

The suture snare 36 and the suture clip 28 can be releasably retained by a retaining member 46. The retaining member 46 can have generally planar longitudinal surfaces and a thickness, or depth (dimension perpendicular to the page in FIG. 1), relative to its major diameter (left-to-right dimension of the retaining member 46 in FIG. 1). The retaining member 46 generally can be made from a flexible material, such as a plastic or rubber material.

The retaining member 46 can be at least generally planar and can define a groove 48 extending about the perimeter of the retaining member 46. In another implementation, the groove 48 can be omitted, and the suture snare 36 releasably retained by the retaining member 46 by another method. For example, the retaining member 46 can have a thickness sufficient to securely receive the suture snare 36, which can be maintained in contact with the retaining member 46 by placing the suture snare 36 under tension. In yet another implementation, the retaining member 46 can be made of a material that is resilient or provides enhanced frictional contact with the suture snare 36.

In at least some aspects of the present disclosure, the suture snare 36 can be released from the retaining member 46 by flexing the retaining member. For example, the suture snare 36 can be removed from the retaining member 46 by applying opposing lateral forces to the distal and proximal ends of the retaining member, by twisting or rotating the retaining member, or similar manipulation. In a further implementation, one or more of the faces 50 of the retaining member 46 can define notches or recesses 52 adjacent one or more portions of the groove 48, which can aid the suture snare 36 in slipping out of engagement with the groove, and thus being released from the retaining member.

As will be described in more detail, the suture 18 can be inserted through the opening in the suture snare 36, and the suture snare can be drawn through the aperture 44 of the suture clip 28 and the aperture 42 of the elongate shaft 26. As the handle 38 continues to move radially outwardly from the elongate shaft 26, the suture 18 can be drawn through the aperture 44 of the suture clip 28 and the aperture 42 of the elongate shaft 26. When the suture 18 extending distally from the distal end 30 of the elongate shaft 26 has reached a desired length, the suture clip 28 can be crimped or otherwise secured against movement relative to the suture 18, and the suture can be cut proximally relative to the suture clip 28.

FIG. 2 is a cross-sectional view of the suture clip delivery device 14. The elongate shaft 26 can include an elongate outer shaft 58 and an elongate inner shaft 60 disposed within a lumen of the outer shaft 58. A crimping assembly 64 can be disposed at the distal end 30 of the elongate outer shaft 58.

The inner shaft 60 can be moveable axially relative to the outer shaft 58. For example, one or more pins 68 may be formed on, or coupled to, the inner shaft and extend radially outwardly therefrom. Each of the one or more pins 68 can be coupled to a distal end of a biasing member 70, such as a spring. When the suture clip delivery device 14 includes more than one pin 68, the suture clip delivery apparatus 14 can include a corresponding number of biasing members 70. In other aspects, the outer shaft 58 and the inner shaft 60 may be configured differently. For example, the outer shaft 58 may be made moveable relative to a fixed inner shaft 60, or both the outer shaft and the inner shaft may be moveable relative to one another.

A proximal end of the biasing member 70 can be coupled to a pivot member 74 that can be disposed about a pin 76. The pin 76 can assist in securing the biasing member 70 within the handle 22, while allowing the pivot member 74 to rotate with respect to the pin. The biasing member 70 can be selected to provide a desired of resistance, and proximally directed force, on the inner shaft 60, when the pivot member 74 is in a resting position.

The pivot member 74 can define a stop 80 configured to engage an edge 82 of the handle 22, which can limit the rotation (counterclockwise, as shown) of the pivot member, and thus distal movement of the inner shaft 60. Similarly, the pivot member 74 can define a notch 88 that can allow for rotation (clockwise, as shown) of the pivot member, and thus proximal movement of the inner shaft 60, until a bottom surface 90 of the notch contacts the edge 82.

In at least some embodiments, the pivot member 74 may be disposed proximally adjacent to a support member 94. The support member 94 can help provide structural integrity to the pivot member 74 during actuation of the actuator 24. The support member 94 can, in at least some implementations, also be used to maintain appropriate resting and actuated positions for the pivot member 74. For example, the support member 94 can be coupled to the handle 22 or shaped so as to limit rotation of the pivot member 74.

The support member 94 can, in some implementations, be coupled to a biasing member 96. The biasing member 96 can be coupled to an aperture 98 of the support member 94 and an anchor 100 coupled to or formed in the handle 22. The biasing member 96 can be selected to apply an opposing biasing force to the biasing member 70. In various examples, the biasing member 96 can be coupled to the support member 94 or the handle 22 in a different manner, or the biasing member 96 can be omitted.

Figure 5:
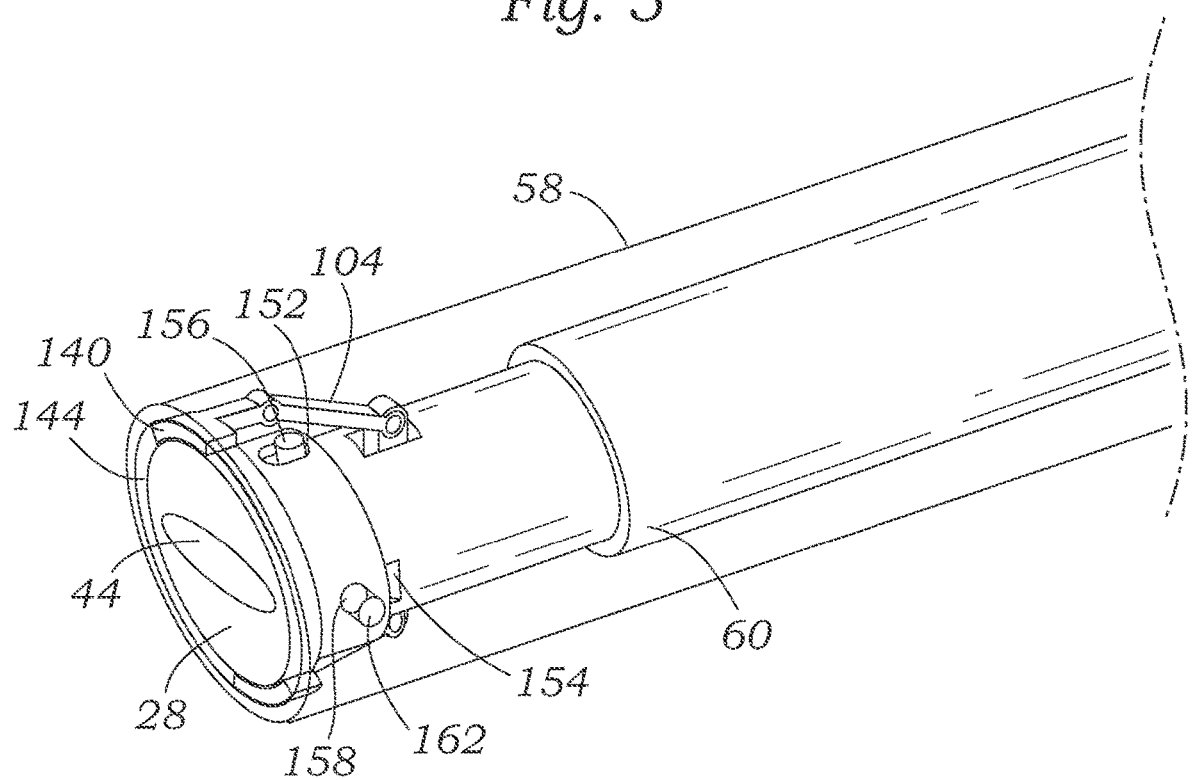
FIG. 5 is perspective view of a crimping assembly portion of the suture clip delivery device of FIG. 1, with an outer surface of the crimping assembly portion shown in transparency.

With reference to FIGS. 3-5, the crimping assembly 64 can include two crimping members 104 disposed partially within apertures 106 formed in the upper and lower radial surfaces of the outer shaft 58. Each of the crimping members 104 can include an inner hinge member 108 and an outer hinge member 110. The inner hinge members 108 can be disposed within triangular recesses 112 formed in the upper and lower radial surfaces of the inner shaft 60, as shown in FIG. 3. The inner hinge members 108 can include an inner aperture 114 formed in the radial surface of the inner hinge members 108. Pins 116 (see FIG. 3) can be inserted through the inner apertures 114 and corresponding inner apertures 118 (see FIG. 4) formed in the radial surfaces of the inner shaft 60.

As shown in FIG. 4, the proximal end of each of the outer hinge members 110 can define a mounting fork 120 configured to receive an outer end of an inner hinge member 108. Apertures 122 can be defined in the lateral surfaces of the mounting fork 120. A pin 124 (FIG. 3) can be inserted through the apertures 122 and an aperture 126 formed in the outer end of an inner hinge member 108.

The outer hinge members 110 can extend into the apertures or recessed portions 106 formed in the outer shaft 58. The outer hinge members 110 can be formed with a bent configuration, where a proximal portion has an obtuse angle relative to the axis of the outer shaft 58, and a distal portion has an acute angle, or is straight, relative to the axis of the outer shaft. Apertures 130 (FIG. 4) can be formed in the radial surfaces of the outer hinge members 110, such as at or proximate an inflection point in the longitudinal surface of the outer hinge members. The outer hinge members 110 can be secured in the apertures or recessed portions 106 by inserting pins 132 (FIG. 3) through the apertures 130 and corresponding apertures 134 formed in the radial surface of the outer shaft 58 (FIG. 4).

The distal ends of the outer hinge members 110 can include jaw portions 140 extending laterally from the sides of the outer hinge members. The jaw portions 140 can be dimensioned to receive the suture clip 28. For example, the jaw portions 140 are shown as arcuate to receive a circular suture clip 28. If the suture clip has non-arcuate edges, or for other reasons, the jaw portions 140 can have non-arcuate shapes, including varying shapes (e.g., jagged or scalloped). The jaw portions 140 can help distribute a compressive force about the radial surface of the suture clip 28. This distribution of force can help close the aperture 44 of the suture clip 28 while reducing bending, buckling, or other types of deformation of the surface of the suture clip. For example, it may be helpful to maintain more flat, or planar, axial surfaces of the suture clip 28, as it may allow the suture clip 28 to be placed flush with devices, such as heart valve repair or replacement prostheses, or help reduce trauma to surrounding tissue by providing an even surface. The distribution of force can also provide for more reliable securement of one or more sutures 18 within the aperture 44, as the compressive forces can be directed to closing the aperture 44, rather than bending the suture clip 28.

The outer shaft 58 can define an annular recessed portion 142 (FIG. 4) surrounding a distal aperture 144 of the outer shaft 58. The jaw portions 140 of the outer hinge members 110 can extend into the annular recessed portion 142. The longitudinal portion of the outer hinge members 110 can extend through notches 146 formed in the upper and lower axial surfaces of the recessed portion 142. The annular recessed portion 142 can be dimensioned to receive a suture clip 28, such that the suture clip 28 can be releasably engaged by the jaw portions 140 of the outer hinge members 110.

The crimping assembly 64 can further include an annular cutting member 150 disposed about the inner shaft 60. The cutting member 150 can include axially elongate, such as oval-shaped, apertures 152 formed in opposing radial surfaces of the cutting member and a radial aperture 158. The apertures 152 can receive pegs 156 radially extending from opposing radial surfaces of the inner shaft 60. The length of the apertures 152 can be longer than the radius of the pegs 156, which can allow the cutting member 150 to move proximally and distally with respect to the inner shaft 60. The radial surface of the cutting member 150 can further define an inner suture aperture 158. The inner suture aperture 158 can be configured to be selectively alignable with a radial aperture 154 of the inner shaft 60 and an outer suture aperture 162 formed in the radial surface of the outer shaft 58. If desired, the sides of the inner suture aperture 158, or the outer suture aperture 162, can be sharpened, such as being provided with a cutting edge, to help sever the suture 18 when it extends through the inner and outer suture apertures 158, 162.

Figure 6:
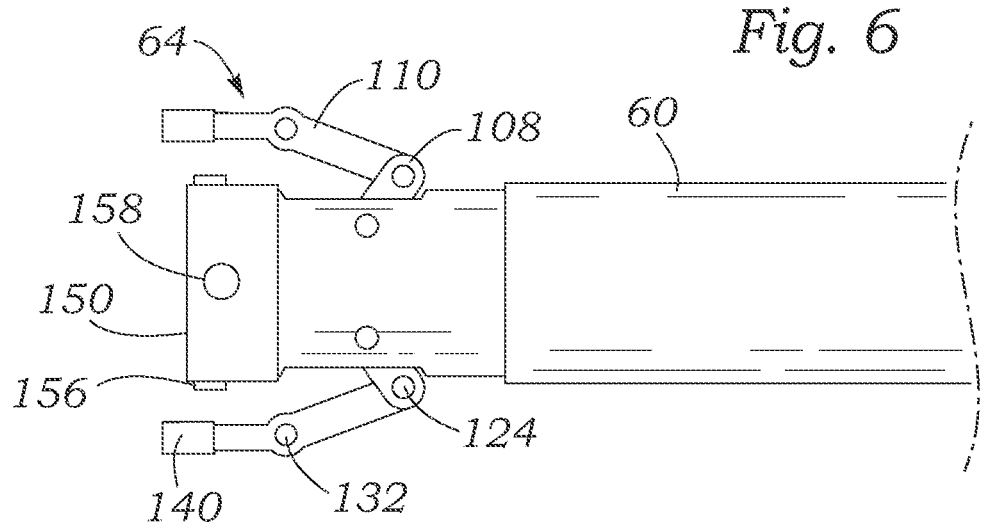
FIG. 6 is an elevational view of components of the crimping assembly of the suture clip delivery device of FIG. 1, showing the crimping assembly in a first position configured to retain a suture clip.
Figure 7:
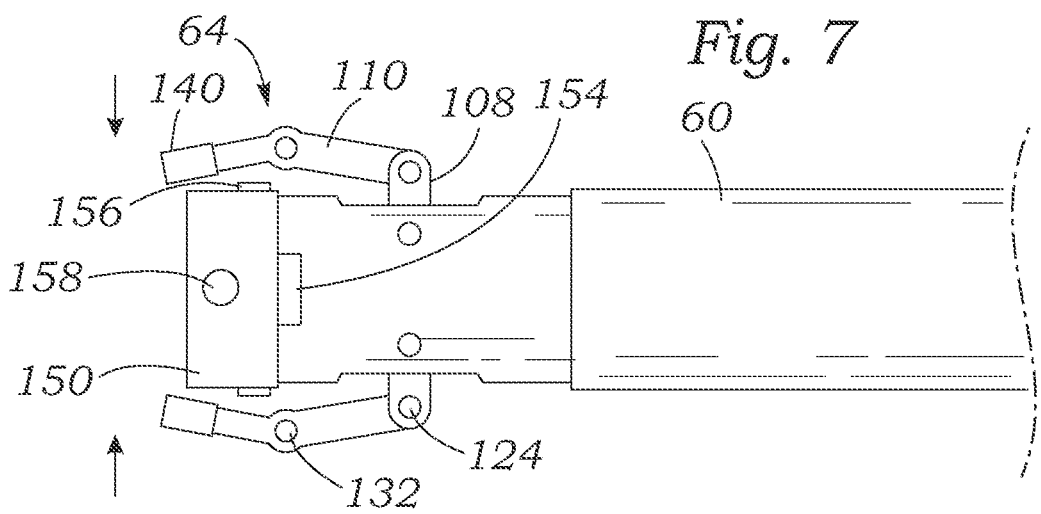
FIG. 7 is an elevational view of components of the crimping assembly of the suture clip delivery device of FIG. 1, showing the crimping assembly in a second position configured to plastically deform a suture clip.
Figure 8:
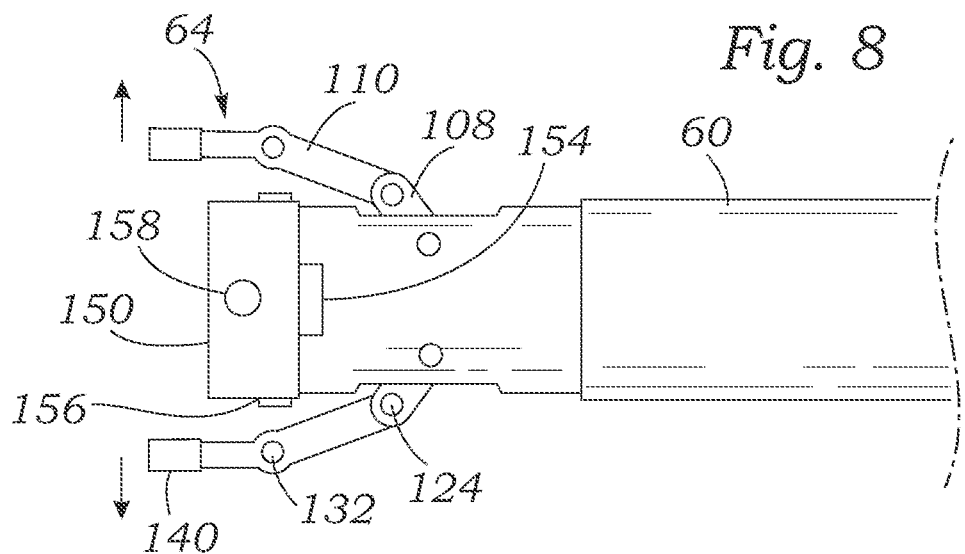
FIG. 8 is an elevational view of components of the crimping assembly of the suture clip delivery device of FIG. 1, showing the crimping assembly in a third position configured to release a suture clip from the crimping assembly and to sever a suture passing through the suture clip.

FIGS. 6-8 illustrate the operation of the crimping assembly 64 as the inner shaft 60 is moved proximally with respect to the outer shaft 58 as the actuator 24 is actuated. FIG. 6 illustrates the crimping assembly 64 in a resting position, prior to actuation of the actuator 24. The inner hinge members 108 can be located proximally within the apertures 112. The outer hinge members 110 can be angled such that, when the inner hinge members 108 are proximally located, the jaw portions 140 of the outer hinge members 110 are biased radially inwardly. When a suture clip 28 is positioned within the jaw portions 140, the jaw portions can exert a radially inwardly directed force, which can help retain the suture clip 28 within the suture clip delivery device 14 while a suture 12 is being inserted proximally into the aperture 44 of the suture clip and radially outwardly through the inner suture aperture 158 and the outer suture aperture 162.

The pegs 156 of the inner shaft 60 can be positioned at distal ends of the apertures 152 of the cutting member 150, which can place the aperture 158 of the cutting member 150 in alignment with the suture aperture 162 of the outer shaft 58. Thus, in the resting position shown in FIG. 6, the crimping assembly 64 can be configured to receive and retain a suture clip 28 within the jaw portions 140 of the outer hinge members 110. A suture 18 can be received through the aperture 44 of the suture clip 28, through the inner suture aperture 158 of the cutting member 150, and radially outwardly through the outer suture aperture 162 of the outer shaft 58.

As shown in FIG. 7, as the inner shaft 60 is moved proximally with respect to the outer shaft 58 (see FIGS. 4 and 5), proximal movement of the pins 116 can cause the inner hinge members 108 to rotate distally about the pins, applying a radially outwardly directed force to the outer hinge members 110 through the pins 124. In turn, the distal ends of the outer hinge members 110 can rotate radially inwardly about the pins 132. As the distal ends of the outer hinge members 110 rotate radially inwardly, the jaw portions 140 can exert a compressive force on the suture clip 28, which can cause the suture clip to plastically deform and the aperture 44 of the suture clip to narrow. If a suture 18 is inserted through the aperture 44, the suture can be secured against movement relative to the suture clip 28 (e.g., FIG. 11). During this initial clamping motion (FIG. 6 to FIG. 7), the pegs 156 of the inner shaft 60 can move proximally relative to the apertures 152 of the cutting member 150. However, the alignment between the inner suture aperture 158 and the outer suture aperture 162 can be maintained.

Referring to FIG. 8, when the inner shaft 60 is moved further proximally from the position of FIG. 7, the inner hinge members 108 can continue to rotate distally about the pins 116. The distal movement of the inner hinge members 108 can cause the inner hinge members to exert a radially inwardly directed force on the outer hinge members 110 through the pins 124, which can cause the distal ends of the outer hinge members 110 to rotate radially outwardly about the pins 132. The radially outward rotation of the distal ends of the outer hinge members 110 can cause the jaw portions 140 to be released from engagement with the suture clip 28, which can allow the suture clip and the suture 18 to be released from the recess 142 of the outer shaft 58.

As the inner shaft 60 moves proximally, the pegs 156 can move proximally within the apertures 152 (e.g., from FIG. 6 to FIG. 7), contacting the proximal lip of the apertures 152. Further proximal motion of the inner shaft 60 (e.g., from FIG. 7 to FIG. 8) causes the cutting member 150 to move proximally along with the inner shaft 60 relative to the outer shaft 58. As the cutting member 150 moves proximally, the inner suture aperture 158 can move proximally with respect to the outer suture aperture 162 (FIG. 5), which can sever a suture 18 inserted through the inner suture aperture 158 and the outer suture aperture 162.

After the actuator 24 is no longer activated, the inner shaft 60 can move distally relative to the outer shaft 58, returning to the resting position illustrated in FIG. 6.

It should be appreciated that changes can be made to the crimping assembly 64 without departing from the scope of the present disclosure. For example, if desired, the cutting member 150 can be configured to cut the suture 18 while the suture aperture 44 is being compressed. Although two crimping members 104 are illustrated, the crimping assembly 64 can include a larger number of crimping members 104, which may be used to further distributed the radially compressive force applied to the suture clip 28. In another example, the crimping assembly 64 can include a single crimping member that is configured to apply a distributed, radially compressive force to the suture clip 28.

Figure 9:
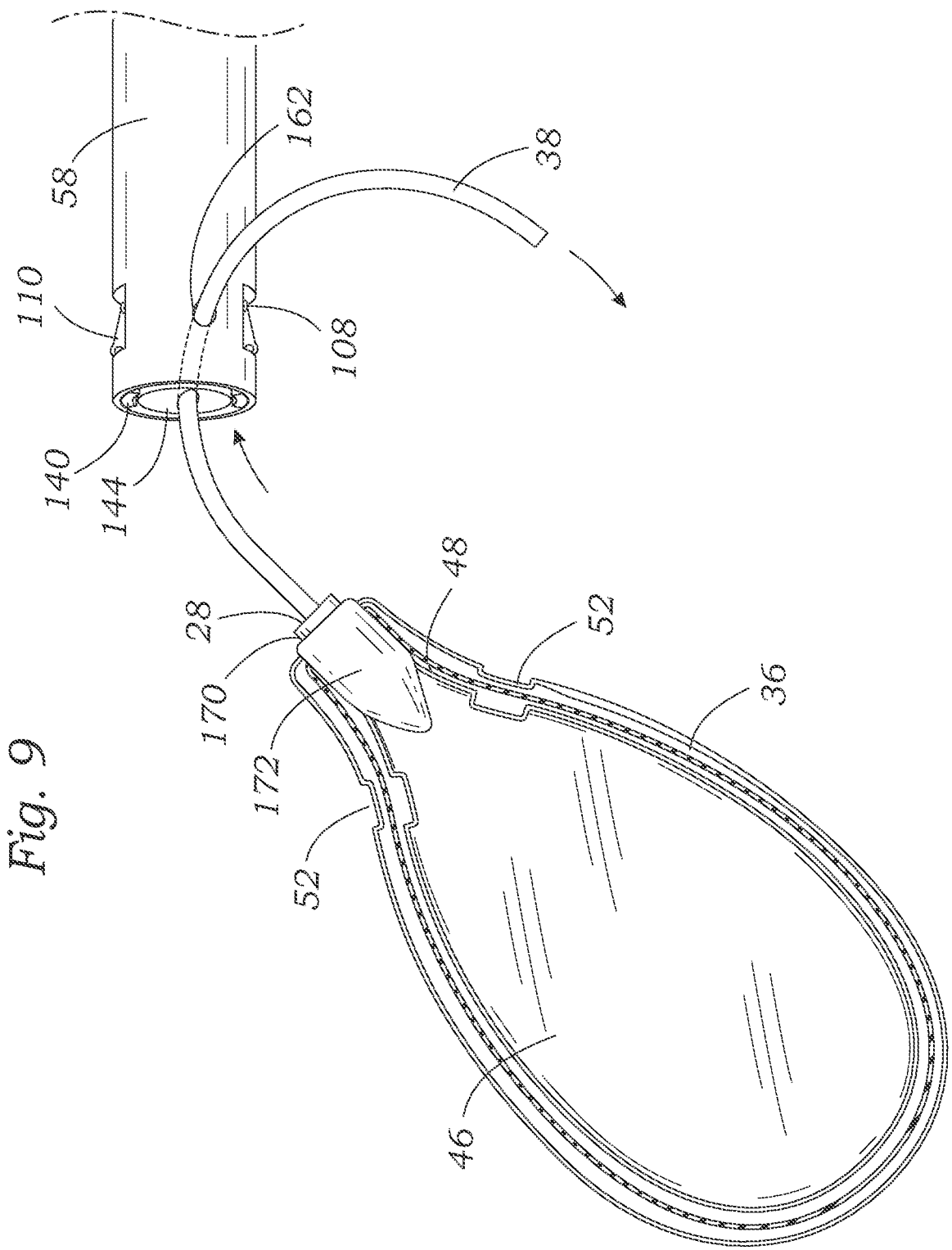
FIG. 9 is a perspective view illustrating the loading of a suture clip into a suture clip delivery device using a suture snare assembly.
Figure 10:
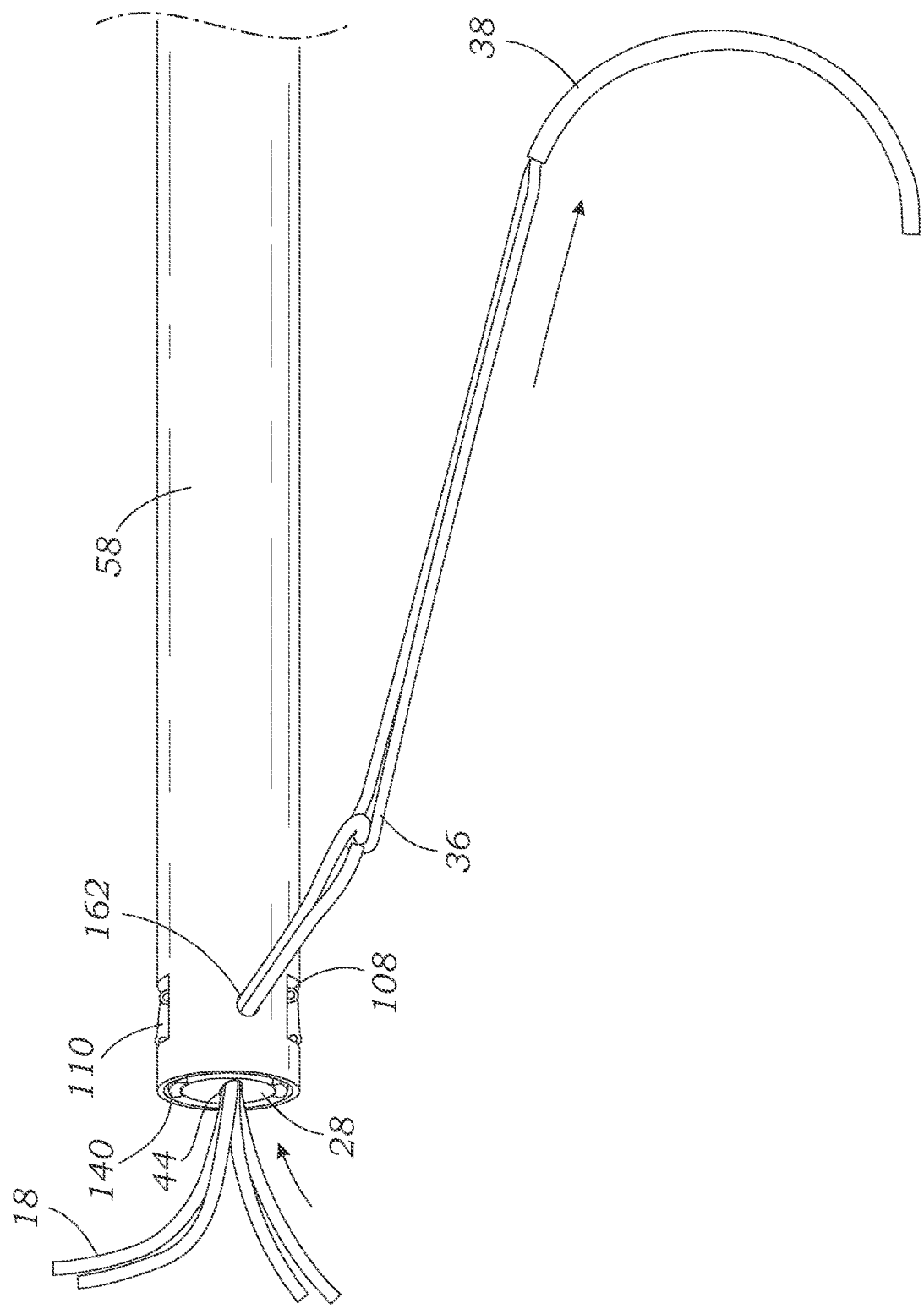
FIG. 10 is a perspective view illustrating the threading of a suture through a suture clip loaded into a suture clip delivery device using a suture snare.

FIGS. 9 and 10 illustrate a method of using the suture clip delivery assembly 10. The handle 38 of the suture snare 36 can be inserted through the aperture 144 in the distal end of the outer shaft 58, through the inner suture aperture 158 (FIG. 4) of the cutting member 150, and radially outwardly through the outer suture aperture 162. As shown in FIG. 9, the suture clip 28 can be in contact with a longitudinal end surface 170 of the retaining member 46. The longitudinal surface 170 can be, at least in some examples, formed on a laterally protruding support member 172. The laterally protruding support member 172 can, for example, help support the suture snare 36, and the groove 48 may extend through the longitudinal surface of the laterally protruding support member 172.

In some cases, the suture clip 28 can rest adjacent the longitudinal surface 170 until the suture clip is inserted into the recess 142 of the outer shaft 58. In other cases, the longitudinal surface 170 can include features to help maintain the suture clip 28 in contact with the retaining member 46. For example, an annular recess (not shown), or a recess otherwise dimensioned to at least partially receive the suture clip 28, may be formed in the longitudinal surface 170. The recess may be configured to exert a slight compressive force on the suture clip 28 in order to retain the suture clip until the suture clip is transferred to the recess 142 of the outer shaft 58 and received within the jaw portions 140 of the outer hinge members 110.

When the suture clip 28 has been transferred into the recess 142, the suture snare 36 can be released from the retaining member 46 by appropriate manipulation, such as flexing, of the retaining member, including releasing the portions of the suture snare proximate the notches 52.

Referring now to FIG. 10, the suture snare 36 can be pulled through the aperture 44 of the suture clip 28, through the inner suture aperture 158 of the cutting member 150, and then radially outwardly through the outer suture aperture 162 of the outer shaft 58. Continued application of a radially outwardly directed force to the handle 38 can pull the suture 18, threaded through the suture snare 36, through the aperture 44 of the suture clip 28, through the inner suture aperture 158 of the cutting member 150, and then radially outwardly through the outer suture aperture 162 of the outer shaft 58.

Figure 11:
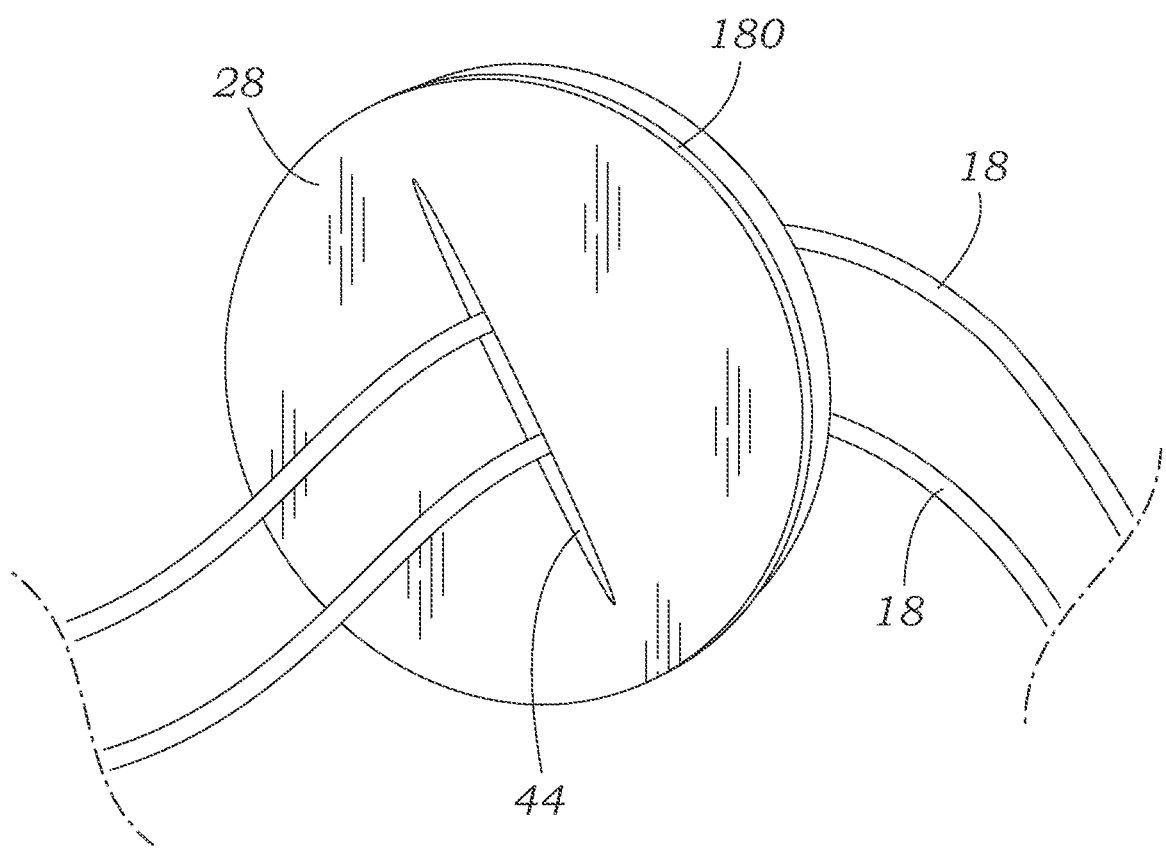
FIG. 11 a perspective view of suture lines secured within a crimped suture clip.

When the suture 18 is at the desired position, such as proximate tissue to be approximated or ligated with the suture, a physician can activate the actuator 24, causing the crimping assembly 64 to crimp the suture clip 28, which can cause the suture clip to plastically deform, reducing the size of the aperture 44, to secure the suture within the suture clip, as described above with reference to FIGS. 6-8, and as illustrated in FIG. 11.

According to a further embodiment, the present disclosure can provide for one or more members to be disposed between tissue to be approximated or ligated with a suture and a suture retaining device such as a suture clip. In a particular implementation, a spacer, such as a bushing, can be disposed between the suture retaining device and the tissue. For example, the bushing can be disposed between a suture clip and the sewing ring of a prosthetic heart valve. Using a spacer intermediate the suture retaining device and the tissue to be approximated or ligated (including a spacer adjacent a medical device to be secured to the tissue) can help provide flexibility about the suture point, particularly if the spacer is formed from a resilient material. In other cases, the spacer can be constructed from a material that has improved biocompatibility compared with the suture retaining device, which can in turn improve the biocompatibility of the suture retaining device. Similarly, the spacer can help reduce trauma to tissue or a medical device proximate the suture retaining device, particularly if the suture retaining device may have any sharp or irregular surfaces.

FIGS. 12 and 13 are generally similar to FIGS. 9 and 10, but include a spacer 190, such as a bushing. In some cases, the spacer 190 can be sized or shaped similarly to the suture clip 28. In other cases, the spacer 190 can have a different size and/or shape than the suture clip 28. In a particular example, a disc-shaped spacer 190 can be used with a non-disc shaped suture clip 28.

With reference to FIG. 12, the spacer 190 can be disposed on the longitudinal end surface 170 of the retaining member 46. The suture clip 28 can be disposed adjacent the spacer 190. The suture clip 28 can then be loaded into the suture clip delivery device 14 as described with respect to FIG. 9.

Referring now to FIG. 13, the suture snare 36 can be pulled through an aperture 192 of the spacer 190, through the aperture 44 of the suture clip 28, through the inner suture aperture 158 of the cutting member 150, and then radially outwardly through the outer suture aperture 162 of the outer shaft 38. As the handle 38 is continued to be moved radially outwardly from the outer shaft 58, the suture 18 can be pulled through the aperture 192 of the spacer 190, through the aperture 44 of the suture clip 28, and through the outer suture aperture 162 of the outer shaft 58 in a similar manner as the handle 38. The suture clip 28 can be crimped and secured to the suture 18 as described above with reference to FIG. 10. Although the suture clip 28 can be maintained within the jaw portions 140 during the process of threading the suture 18 through the suture clip 28 and suture clip delivery device 14, the spacer 190 can remain outside of the jaw portions 140, and thus can be moveable over the suture snare 36 and the suture while the suture clip is being crimped to the suture.

FIGS. 14A-14G illustrate plan views of various examples of suture clips 28 that may be used with the suture clip delivery device 14. Generally, the suture clips 28 can have a thin thickness, or depth, (dimension perpendicular to the page in FIGS. 14A-14G) relative to their major dimension, or diameter. The thickness can be relatively uniform for the whole suture clip 28, and can be substantially smaller relative to the diameter of the suture clip 28 (left-to-right dimension in FIGS. 14A-14G), such as less than 25% of the diameter, less than about 15% of the diameter, less than about 10% of the diameter, and/or less than about 5% of the diameter.

The suture clips 28, and other suture clip embodiments, can be made from a variety of materials including, for example, stainless steel, titanium, titanium alloys or other metal alloys, various plastics, and other biologically-compatible materials.

Figure 14A:
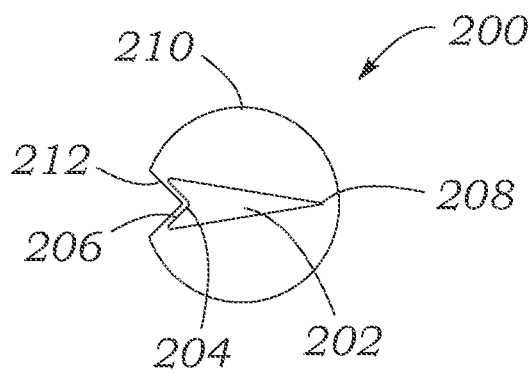
FIG. 14A is a plan view of a suture clip according to an embodiment of the present disclosure.

The suture clip 200 of FIG. 14A can include a tapered aperture 202 with a notch 204 formed in a first end 206 of the aperture 202, the first end of the aperture being wider than, and tapering to, a second end 208 of the aperture. The outer radial surface 210 of the suture clip 200 can include a notch 212 proximate to, and nested within, the notch 204 of the aperture 202. The notches 204, 212 can make the side of the suture clip 200 proximate the notches 204, 212 more susceptible to being bent or radially compressed when compressive forces are applied to radial sides of the suture clip 200, perpendicular to the longitudinal axis of the aperture 202.

Figure 14B:
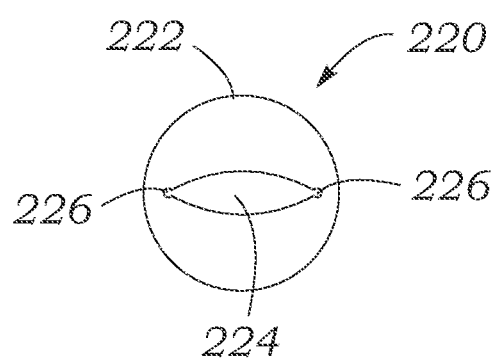
FIG. 14B is a plan view of a suture clip according to an embodiment of the present disclosure.

FIG. 14B illustrates a suture clip 220 that can have a generally circular outer surface 222 and defines a generally elliptical aperture 224, with arcuate or rounded portions 226 defined at the vertices of the aperture. The arcuate portions 226 can help reduce stress at the vertices of the aperture 224 when the suture clip 220 is crimped.

Figure 14C:
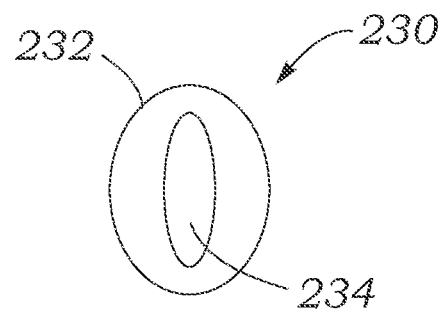
FIG. 14C is a plan view of a suture clip according to an embodiment of the present disclosure.

The suture clip 230 of FIG. 14C can have an at least generally elliptical radial outer surface 232 and can define an at least generally elliptical aperture 234. The at least generally elliptical radial outer surface 232 can allow the suture clip 230 be crimped with lower compressive forces than, for example, suture clips 28 having a circular shape.

Figure 14D:
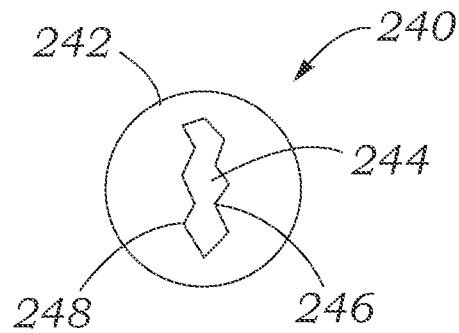
FIG. 14D is a plan view of a suture clip according to an embodiment of the present disclosure.

FIG. 14D illustrates a suture clip 240 that can have an at least generally circular outer surface 242 and defines an aperture 244 that can have an irregular or jagged perimeter including angled protruding sections 246 and angled recesses 248. When crimped, the angled protruding sections 246 and angled recessed portions 248 can be placed into contact with one another, which can provide a roughened surface or tortuous path that can help prevent the suture 18 from slipping axially or radially with respect to the suture clip 240.

Figure 14E:
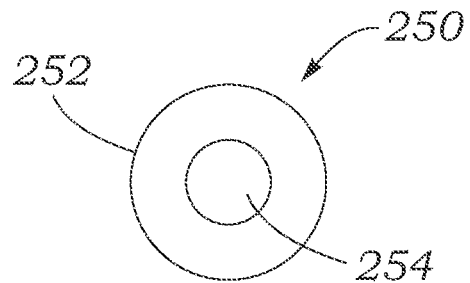
FIG. 14E is a plan view of a suture clip according to an embodiment of the present disclosure.

The suture clip 250 of FIG. 14E can have a generally annular radial surface 252 defining a generally annular aperture 254. The diameter of the aperture 254 can be selected to provide a desired degree of resistance to crimping of the suture clip 250. That is, a larger diameter aperture 254 may be easier to crimp, as there can be less material to deform.

Figure 14G:
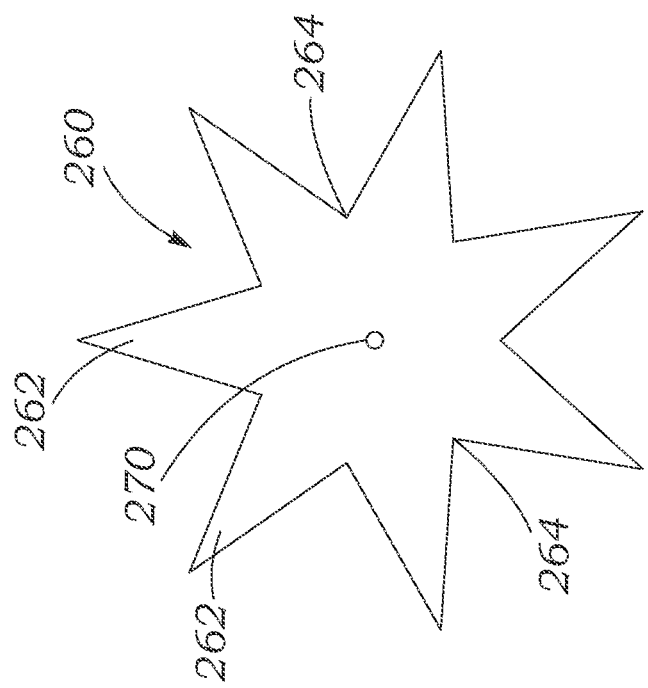
FIG. 14G is a plan view of the star-shaped suture clip of FIG. 14F in a crimped state.
Figure 14F:
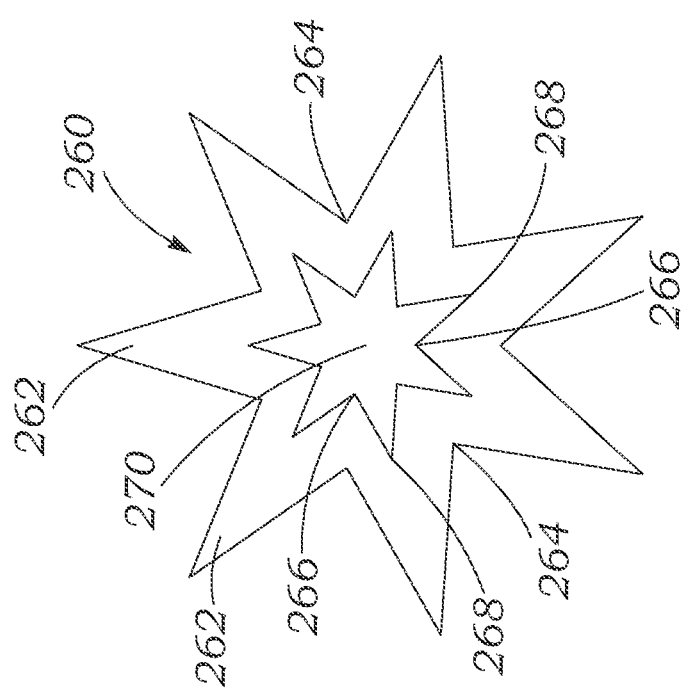
FIG. 14F is a plan view of a star-shaped suture clip in an uncrimped state according to an embodiment of the present disclosure.

A star-shaped suture clip 260 is shown in FIG. 14F. The suture clip 260 can define a plurality of outer triangular points 262 and corresponding outer triangular recesses 264, and a plurality of inner triangular points 266 and corresponding triangular recesses 268 of a central aperture 270. As shown, each of the outer triangular points 262 is aligned with an inner triangular recess 268. Similarly, each of the outer triangular recesses 264 is aligned with an inner triangular point 266. Although the suture clip 260 is shown with seven outer triangular points 262, outer triangular recesses 264, inner triangular points 266, and outer triangular recesses 268, in other implementations, the suture clip 260 can have another number of points 262, 266 and/or recesses 264, 268. In addition, the shape of the suture clip 260 can be varied, such as having scalloped, rather than triangular, points and recesses.

When used with the crimping assembly 64 (e.g., FIGS. 3-4), the jaw portions 140 can be shaped to apply a radially-inwardly directed crimping force to the outer triangular recesses 264, and in turn to the inner triangular points 266. FIG. 14G illustrates the suture clip 260 in a crimped state. As the crimping force is applied, the width of the inner triangular recesses 268 can reduce, which can trap suture 18 in the inner triangular recesses, or within the central aperture 270 of the suture clip 260. The size of the central aperture 270 can also be reduced as the crimping force is applied to the suture clip 260. The pattern of the points 262, 266 and recesses 264, 268 can facilitate crimping of the suture clip 260, as well as allowing the suture clip to be compressed symmetrically.

Figure 15:
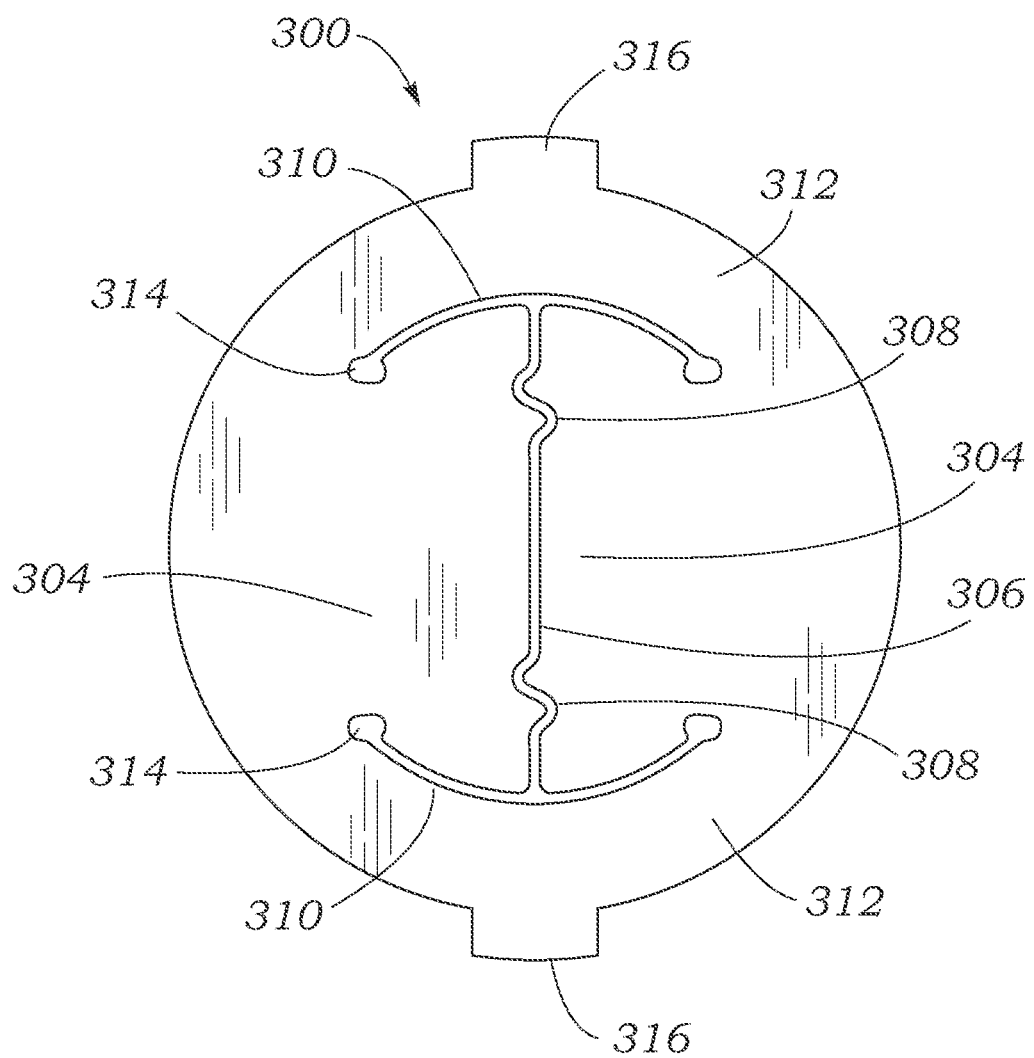
FIG. 15 is a plan view of a suture clip according to an embodiment of the present disclosure.

FIG. 15 illustrates an embodiment of a suture clip 300 shown in a crimped state, or otherwise configured to secure a suture 18. The suture clip 300 can be generally disk shaped with two suture engagement flaps 304 that project inwardly toward each other and define a suture engagement slot 306. The suture engagement slot 306 can include a tortuous portion 308 at either end to prevent sutures that are pinched between the flaps 304 in the suture engagement slot 306 from sliding laterally out of the slot into either of the arcuate slots 310 that extend from the ends of the slot. The arcuate slots 310 space the flaps 304 from an outer annular portion 312 of the clip 300 and allow the flaps 304 to articulate out of the plane of FIG. 15 while the outer annular portion 312 stays generally in or near the plane of the FIG. 15. The arcuate slots 310 can include enlarged, rounded end portions 314 that can reduce stress concentrations in the clip material around them when the flaps 304 are resiliently deformed out of plane. FIG. 15 also shows two tabs 316 at diametrically opposite sides of the clip 300.

In some embodiments, the suture clips 300 can be formed from nitinol (e.g., with an alloy of nickel at about 54.5-57% by weight with titanium accounting for the balance except for residual amounts (less than 0.05% each) of oxygen, carbon, and hydrogen) or another shape memory and/or pseudoelastic material, with the suture clips 300 formed so that the clip assumes its closed position (e.g., the flat position shown in FIG. 15) when in the austenite condition (e.g., when generally unstressed at body temperature). The nitinol can have an austenite finish temperature selected to match the particular application. For example, an austenite finish temperature of from about −5 degrees to about +15 degrees Celsius may be selected.

A suture clip, such as the suture clip 300, can be formed from material that will assume its martensite condition when subjected to sufficient stress, such as the stress applied to the clip's engagement flaps 304 and annular outer body 312 when the suture clip 300 is mounted for deployment. In such an embodiment, the stress applied to the engagement flaps 304 can be sufficient to force the engagement flaps to open wide enough to allow one or more suture lines through the slot 306. The stressed material, including the bent material where the engagement flaps 304 join the annular outer body 312, is forced into its martensite condition. When the stress is removed, such as when the clip 300 is deployed, the material can return to its austenite condition so that the annular outer body 312 and the engagement flaps 304 can assume their flat shape shown in FIG. 15.

According to another aspect, the present disclosure provides suture retaining devices, such as clips, that can have atraumatic or biocompatible properties. These suture retaining devices can include, for example, a suture clip 28 as previously described (e.g., the suture clips 200, 220, 230, 240, 250, 260 of FIGS. 14A-14G), the suture clip 300 (FIG. 15), or other types of suture clips or suture securing or retaining devices, including crimp able cylinders or suture retaining devices made from plastically deformable materials, or from shape memory and/or pseudoelastic materials, such as nitinol. Suitable suture retaining devices are disclosed in U.S. Pat. Nos. 6,626,930; 9,017,347; 8,753,373; 8,777,968; 7,628,797; U.S. Patent Application Publication No. US 2007/0005079 A1; and U.S. Patent Application Publication No. US 2014/0031864 A1; the entire contents of each of these documents are expressly incorporated by reference. FIG. 11 illustrates a suture clip 28 having an atraumatic or biocompatible coating 180.

According to one implementation, the suture retaining devices can be coated with a polymer that can help reduce trauma to tissues placed into contact with a suture retaining device or improve the biocompatibility of the suture retaining device, such as by making the surface of the suture retaining device less rigid. The polymer can be a biocompatible polymer, including various types of medical grade elastomers. Suitable elastomers can include silicone rubbers, for example, a siloxane polymer such as a polydimethylsiloxane polymer, a medical grade olefin-based elastomer, or copolymers, such as ethyl vinyl acetate. In specific examples, the polymer is a silicone elastomer, for example SILASTIC® (Dow Corning Corp., Midland, Mich.) polymer. In other examples, the polymer can be a fluorinated polymer, such as poly(tetrafluoroethylene) (PTFE). When a suture clip 28 is used with a spacer 190, the spacer 190 may be formed from, or coated with, a biocompatible polymer, instead of, or in addition to, coating or treating the suture clip 28.

The polymer can be applied in various forms, including coatings of various thicknesses, in expanded forms (such as ePTFE), including felts or pillows. In a specific example, the suture retaining device can be fully or partially encapsulated by the polymer, such as being encapsulated by a pillow formed from the polymer. In some cases, the encapsulating material can be secured to the suture retaining device in a manner than does not inhibit suture access to a suture aperture of the suture retaining device. For example, the encapsulating material can be secured to suture retaining device about the perimeter of the suture aperture. In another example, the encapsulating material can be bonded to the suture retaining device, and one or more slits aligned with the suture aperture may be formed in the encapsulating material.

Figure 16A:
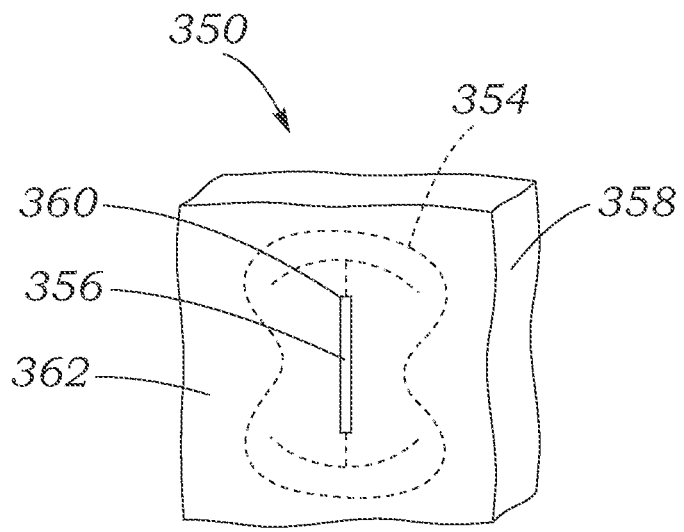
FIG. 16A is an elevational view of an encapsulated suture clip according to an embodiment of the present disclosure.
Figure 16B:
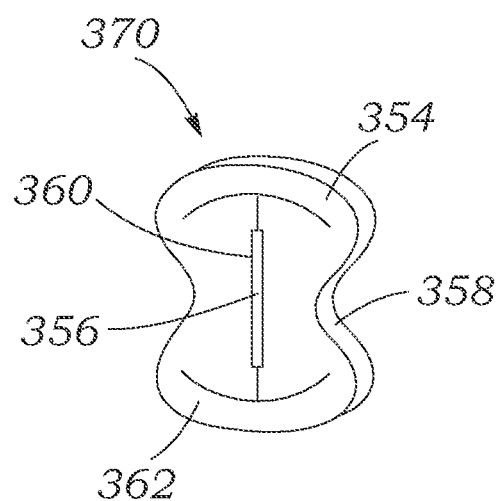
FIG. 16B is an elevational view of an encapsulated suture clip according to an embodiment of the present disclosure.

FIG. 16A illustrates an encapsulated suture retaining device 350. The encapsulated suture retaining device 350 can include a suture retaining device 354 defining a suture aperture 356. The suture retaining device 354 can be surrounded by a layer of encapsulating material 358. The encapsulating material 358 can be bonded to the suture retaining device 354, such as being mechanically, chemically, or thermally bonded to the suture retaining device. One or more slits 360 can be formed in the faces 362 of the encapsulating material 354, such as a slit being formed in each face. The slits 360 can cooperate with the suture aperture 356 to define an opening through which one or more sutures may pass. If desired, excess encapsulating material 354 may be trimmed, such as shown in the encapsulated suture retaining device 370 of FIG. 16B, which can be otherwise similar to the encapsulated suture retaining device 350 of FIG. 16A.

According to one method of forming an encapsulated suture retaining device, such as the encapsulated suture retaining device 350 or the encapsulated suture retaining device 370, a suture retaining device can be placed on a layer of encapsulating material. The encapsulating material can be folded over the suture retaining device. Alternatively, the suture retaining device can be inserted into a pouch of encapsulating material.

The edges of the encapsulating material, such as an end of a pouch or edges of folded encapsulating material, can be sealed to fully encapsulate the suture retaining device. Suitable sealing methods include mechanical, thermal, or chemical sealing. For example, edges of the encapsulating material can be sealed together, and optionally to surfaces of the suture retaining device, using an adhesive.

A slit can be formed in the encapsulating material to cooperate with an aperture of the suture retaining device to define an opening through which one or more lines of suture material may be inserted. Optionally, excess encapsulating material can be trimmed so that the encapsulated suture retaining device is dimensioned more similarly to a non-encapsulated suture retaining device, which may be useful, for example, in using an encapsulated suture retaining device with a suture retaining device delivery device.

In another implementation, the suture retaining devices can be coated or otherwise treated with a polymer or other material to improve biocompatibility, including hemocompatibility. For example, a suture retaining device can be treated with a material that can repel materials that might foul the surface of the suture retaining device, such as proteins, platelets, or cells, and be nonthrombogenic. One suitable class of materials can be hydrogel materials. The surface treatment can include biological materials, including biological materials to help the suture retaining device be nonthrombogenic, to encourage tissue ingrowth to help the suture retaining device become incorporated into surrounding tissue, or to otherwise improve biocompatibility. When a suture clip 28 is used with a spacer 190, the spacer 190 can be coated or otherwise treated with such a biocompatible material, in addition to, or instead of, coating the suture clip 28.

In a particular example, the suture retaining device can be coated with heparin or a material that incorporates heparin. For example, heparin, or components thereof, may be incorporated into a polymer that is then used to surface treat the suture retaining device. In other examples, the surface treatment can include treatment with an extracellular matrix (such as from a decellularized tissue scaffold) or components of the extracellular matrix, such as heparin, chondroitin, keratin, hyaluronic acid, collagen, elastin, fibronectin, laminin, or galectin.

In particular implementations, the suture retaining device can be coated with multiple materials. For example, a first polymer may be coated with a second polymer, where the second polymer can improve the biocompatibility of the first polymer. In a further example, the first or second polymer can incorporate a biologically active material, such as heparin. In yet another example, a polymer can be coated with a biologically active material, such as heparin, one or components of the extracellular matrix, an extracellular matrix, or combinations thereof.

In some implementations, surface treatments can be applied to a portion of a suture retaining device, such as to one side of a suture clip. In further implementations, surface treatments can be applied to multiple portions, or all, of the suture retaining device, such as both sides of a suture clip. When surface treatments are applied to multiple portions of a suture retaining device, the surfaces treatments can be the same, in some examples, while in other examples the surface treatments can be different.

The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology. We therefore claim all that comes within the scope of the following claims.

What is claimed is:

1. A device for deploying a suture clip onto a suture, comprising:
    a proximal handle portion comprising an actuator;
    an outer shaft defining an inner lumen;
    an inner shaft at least partially disposed within the inner lumen of the outer shaft and axially moveable relative to the outer shaft; and
    a crimping assembly disposed at least partially within a distal end of the outer shaft, the crimping assembly comprising a plurality of opposed crimping members pivotably coupled to the inner shaft and configured to receive and radially compress the suture clip, wherein each crimping member of the plurality of opposed crimping members defines a distal jaw portion, the distal jaw portion of each crimping member of the plurality of opposed crimping members being configured to receive and radially compress the suture clip and being at least partially disposed within the inner lumen of the distal end of the outer shaft;
    wherein the actuator is configured to axially move the inner shaft relative to the outer shaft such that the plurality of opposed crimping members move radially inwardly from a first position where the plurality of opposed crimping members are configured to receive the suture clip to a second position where the plurality of opposed crimping members are configured to radially compress the suture clip, causing the suture clip to plastically deform, wherein the distal jaw portion of each crimping member of the plurality of opposed crimping member is located at least partially within the outer shaft when the plurality of opposed crimping members are in the second position.

2. The device of claim 1, wherein the actuator is configured to move the inner shaft axially, proximally or distally, relative to the outer shaft.

3. The device of claim 1, wherein the plurality of opposed crimping members are articulated, each crimping member of the plurality of opposed crimping members comprising an inner hinge member pivotably coupled to an outer hinge member.

4. The device of claim 1, wherein the plurality of opposed crimping members are disposed proximate to opposing sides of the distal end of the outer shaft.

5. The device of claim 1, the crimping assembly further comprising a cutting member.

6. The device of claim 1, wherein the device is configured to crimp a disk-shaped suture clip.

7. The device of claim 1, in combination with:
    the suture clip; and
    a suture snare assembly comprising:
        a suture snare comprising a snare loop coupled to a handle; and
        a generally planar retainer surface configured to releasably retain the suture snare.

8. The device of claim 1, wherein the distal end of the outer shaft defines an axially recessed portion configured to receive the suture clip.

9. The device of claim 1, wherein each crimping member of the plurality of opposed crimping members comprises an inner crimping member pivotably coupled to an outer crimping member.

10. The device of claim 9, wherein the inner crimping members are pivotably coupled to the inner shaft.

11. The device of claim 10, wherein a first longitudinal end of at least one inner crimping member is pivotably coupled to the inner shaft and a second, opposing, longitudinal end of the inner crimping member is pivotably coupled to the outer crimping member.

12. The device of claim 11, wherein the inner crimping member extends through an aperture formed in the inner shaft.

13. The device of claim 10, wherein the outer crimping members are pivotably coupled to the outer shaft.

14. The device of claim 9, wherein the outer crimping members are pivotably coupled to the outer shaft.

15. A device for deploying a suture clip onto a suture, comprising:
    a proximal handle portion comprising an actuator;
    an outer shaft defining an inner lumen;
    an inner shaft at least partially disposed within the inner lumen of the outer shaft and axially moveable relative to the outer shaft; and
    a crimping assembly disposed at least partially within a distal end of the outer shaft, the crimping assembly comprising (1) a plurality of opposed crimping members pivotably coupled to the inner shaft and configured to receive and radially compress the suture clip, wherein each crimping member of the plurality of opposed crimping members defines a distal jaw portion, the distal jaw portion of each crimping member of the plurality of opposed crimping members being configured to receive and radially compress the suture clip and being at least partially disposed within the inner lumen of the distal end of the outer shaft; and (2) a cutting member;
    wherein the actuator is configured to axially move the inner shaft relative to the outer shaft such that the plurality of opposed crimping members move radially inwardly from a first position where the plurality of opposed crimping members are configured to receive the suture clip to a second position where the plurality of opposed crimping members are configured to radially compress the suture clip, causing the suture clip to plastically deform.

16. The device of claim 15, wherein the cutting member comprises an annular body defining axial and radial apertures for receiving the suture.

17. The device of claim 15, wherein:
    (1) a radial surface of the outer shaft defines an outer suture aperture and the inner shaft defines a plurality of radially extending pegs; and (2) the cutting member is disposed about the inner shaft, a radial surface of the cutting member defining a plurality of positioning apertures configured to receive the plurality of radially extending pegs and an inner suture aperture configured to receive the suture, wherein the plurality of positioning apertures have an axial length larger than a diameter of the plurality of radially extending pegs and the cutting member is axially moveable from a first position where the inner suture aperture and the outer suture aperture are aligned to a second position where the inner suture aperture and the outer suture aperture are not aligned.

18. A suture clip delivery assembly comprising:
a device for deploying a suture clip onto a suture, the device comprising:
   a proximal handle portion comprising an actuator;
   an outer shaft defining an inner lumen;
   an inner shaft at least partially disposed within the inner lumen of the outer shaft and axially moveable relative to the outer shaft; and
   a crimping assembly disposed at least partially within a distal end of the outer shaft, the crimping assembly comprising a plurality of opposed crimping members pivotably coupled to the inner shaft and configured to receive and radially compress the suture clip, wherein each crimping member of the plurality of opposed crimping members defines a distal jaw portion, the distal jaw portion of each crimping member of the plurality of opposed crimping members being configured to receive and radially compress the suture clip and being at least partially disposed within the inner lumen of the distal end of the outer shaft;
   wherein the actuator is configured to axially move the inner shaft relative to the outer shaft such that the plurality of opposed crimping members move radially inwardly from a first position where the plurality of opposed crimping members are configured to receive the suture clip to a second position where the plurality of opposed crimping members are configured to radially compress the suture clip, causing the suture clip to plastically deform;
a suture clip; and
a suture snare assembly comprising:
   a suture snare comprising a snare loop coupled to a handle; and
   a generally planar retainer surface configured to releasably retain the suture snare.

19. A device for deploying a suture clip onto a suture, comprising:
a proximal handle portion comprising an actuator;
an outer shaft defining an inner lumen;
an inner shaft at least partially disposed within the inner lumen of the outer shaft and axially moveable relative to the outer shaft; and
a crimping assembly disposed at least partially within a distal end of the outer shaft, the crimping assembly comprising a plurality of opposed crimping members pivotably coupled to the inner shaft and configured to receive and radially compress the suture clip, wherein:
(1) each crimping member of the plurality of opposed crimping members defines a distal jaw portion, the distal jaw portion of each crimping member of the plurality of opposed crimping members being configured to receive and radially compress the suture clip and being at least partially disposed within the inner lumen of the distal end of the outer shaft; and
(2) the distal end of the outer shaft defines an axially recessed portion configured to receive the suture clip; and
wherein the actuator is configured to axially move the inner shaft relative to the outer shaft such that the plurality of opposed crimping members move radially inwardly from a first position where the plurality of opposed crimping members are configured to receive the suture clip to a second position where the plurality of opposed crimping members are configured to radially compress the suture clip, causing the suture clip to plastically deform.

20. A device for deploying a suture clip onto a suture, comprising:
a proximal handle portion comprising an actuator;
an outer shaft defining an inner lumen;
an inner shaft at least partially disposed within the inner lumen of the outer shaft and axially moveable relative to the outer shaft; and
a crimping assembly disposed at least partially within a distal end of the outer shaft, the crimping assembly comprising a plurality of opposed crimping members pivotably coupled to the inner shaft and configured to receive and radially compress the suture clip, wherein:
(1) each crimping member of the plurality of opposed crimping members defines a distal jaw portion, the distal jaw portion of each crimping member of the plurality of opposed crimping members being configured to receive and radially compress the suture clip and being at least partially disposed within the inner lumen of the distal end of the outer shaft;
(2) each crimping member of the plurality of opposed crimping members comprises an inner crimping member pivotably coupled to an outer crimping member and the inner crimping members are pivotably coupled to the inner shaft; and
(3) a first longitudinal end of at least one inner crimping member is pivotably coupled to the inner shaft and a second, opposing, longitudinal end of the inner crimping member is pivotably coupled to the outer crimping member and the at least one inner crimping member extends through an aperture formed in the inner shaft; and
wherein the actuator is configured to axially move the inner shaft relative to the outer shaft such that the plurality of opposed crimping members move radially inwardly from a first position where the plurality of opposed crimping members are configured to receive the suture clip to a second position where the plurality of opposed crimping members are configured to radially compress the suture clip, causing the suture clip to plastically deform.

21. The device of claim 20, wherein an outer crimping member to which the inner crimping member is pivotably coupled is pivotably coupled to the outer shaft at an aperture formed in the outer shaft.

22. The device of claim 21, wherein a radial surface of the outer shaft defines an outer suture aperture, the outer suture aperture being different than the aperture to which the outer crimping member is coupled, and the inner shaft defines a plurality of radially extending pegs, the device further comprising:
a cutting member disposed about the inner shaft, a radial surface of the cutting member defining a plurality of positioning apertures configured to receive the plurality of radially extending pegs and an inner suture aperture configured to receive the suture, wherein the plurality of positioning apertures have an axial length larger than a diameter of the plurality of radially extending pegs and the cutting member is axially moveable from a first position where the inner suture aperture and the outer suture aperture are aligned to a second position where the inner suture aperture and the outer suture aperture are not aligned.

23. A device for deploying a suture clip onto a suture, comprising:

a proximal handle portion comprising an actuator;

an outer shaft defining an inner lumen;

an inner shaft at least partially disposed within the inner lumen of the outer shaft and axially moveable relative to the outer shaft; and a crimping assembly disposed at least partially within a distal end of the outer shaft, the crimping assembly comprising a plurality of opposed crimping members pivotably coupled to the inner shaft and configured to receive and radially compress the suture clip, wherein:

(1) each crimping member of the plurality of opposed crimping members defines a distal jaw portion, the distal jaw portion of each crimping member of the plurality of opposed crimping members being configured to receive and radially compress the suture clip and being at least partially disposed within the inner lumen of the distal end of the outer shaft;

(2) each crimping member of the plurality of opposed crimping members comprises an inner crimping member pivotably coupled to an outer crimping member; and (3) the outer crimping members are pivotably coupled to the outer shaft; and wherein the actuator is configured to axially move the inner shaft relative to the outer shaft such that the plurality of opposed crimping members move radially inwardly from a first position where the plurality of opposed crimping members are configured to receive the suture clip to a second position where the plurality of opposed crimping members are configured to radially compress the suture clip, causing the suture clip to plastically deform.

24. A device for deploying a suture clip onto a suture, comprising:

a proximal handle portion comprising an actuator;

an outer shaft defining an inner lumen;

an inner shaft at least partially disposed within the inner lumen of the outer shaft and axially moveable relative to the outer shaft; and a crimping assembly disposed at least partially within a distal end of the outer shaft, the crimping assembly comprising a plurality of opposed crimping members pivotably coupled to the inner shaft and configured to receive and radially compress the suture clip, wherein:

(1) each crimping member of the plurality of opposed crimping members defines a distal jaw portion, the distal jaw portion of each crimping member of the plurality of opposed crimping members being configured to receive and radially compress the suture clip and being at least partially disposed within the inner lumen of the distal end of the outershaft; and (2) each crimping member of the plurality of opposed crimping members comprises an inner crimping member pivotably coupled to an outer crimping member and pivotably coupled to the inner shaft, wherein the outer crimping member is pivotably coupled to the outer shaft; and wherein the actuator is configured to axially move the inner shaft relative to the outer shaft such that the plurality of opposed crimping members move radially inwardly from a first position where the plurality of opposed crimping members are configured to receive the suture clip to a second position where the plurality of opposed crimping members are configured to radially compress the suture clip, causing the suture clip to plastically deform.

\* \* \* \* \*